US012702524B2

(12) United States Patent
Savage et al.

(10) Patent No.: US 12,702,524 B2
(45) Date of Patent: Aug. 11, 2026

(54) TEMPLATE AND METHOD FOR REMOVING A TATTOO THROUGH PATTERNED TRANS-EPIDERMAL PIGMENT RELEASE

(71) Applicant: Rejuvatek Medical Inc., Sandy, UT (US)

(72) Inventors: Jack H. Savage, Sandy, UT (US); Timothy N. Turner, West Jordan, UT (US); Gregg D. Niven, Kaysville, UT (US)

(73) Assignee: Rejuvatek Medical Inc., Sandy, UT (US)

( * ) Notice: Subject to any disclaimer, the term of this patent is extended or adjusted under 35 U.S.C. 154(b) by 1119 days.

(21) Appl. No.: 17/115,568

(22) Filed: Dec. 8, 2020

(65) Prior Publication Data

US 2021/0113296 A1 Apr. 22, 2021

Related U.S. Application Data

(63) Continuation-in-part of application No. 16/707,865, filed on Dec. 9, 2019, now Pat. No. 11,771,877,
(Continued)

(51) Int. Cl.
*A61B 17/00* (2006.01)
*A61B 90/00* (2016.01)
(Continued)

(52) U.S. Cl.
CPC .............. *A61B 90/39* (2016.02); *A61B 17/00* (2013.01); *A61F 7/00* (2013.01);
(Continued)

(58) Field of Classification Search
CPC ................ A61M 37/0015; A61M 5/46; A61M 2037/003; A61B 90/39; A61B 2017/00769; A61B 2017/00951; A61B 2090/395
See application file for complete search history.

(56) References Cited

U.S. PATENT DOCUMENTS 4,967,203 A 10/1990 Doan et al.
5,971,763 A 10/1999 Yau
(Continued)

FOREIGN PATENT DOCUMENTS

TW 304872 B 5/1997
WO 2012099563 A1 7/2012

OTHER PUBLICATIONS

Extended European Search Report; European Patent Application No. 23155577.2; Rejuvatek Medical Inc.; dated Mar. 31, 2023.
(Continued)

*Primary Examiner* — Jessica Arble
(74) *Attorney, Agent, or Firm* — SandBright Intellectual Property; Robert D. Spendlove

(57) ABSTRACT

Embodiments of a method for removing a tattoo through patterned trans-epidermal pigment release includes determining first treatment area of skin of a patient through a primary template including primary apertures, marking the first treatment area of skin of the patient along borders of the primary apertures to outline a grid of primary tegulae, and delivering a tattoo removal fluid to the marked first exposed skin. In an alternate embodiment, a template, which may be adhered to the skin, is used during a disruption process to create a structured, patterned procedure to remove skin irregularities. The template has a plurality of needle apertures, an adhesive layer, and a release liner. The release liner may be removed, exposing the adhesive layer, so that the
(Continued)

template, with the plurality of needle apertures, may be positioned over the skin irregularity.

21 Claims, 22 Drawing Sheets

Related U.S. Application Data which is a continuation-in-part of application No. 15/261,670, filed on Sep. 9, 2016, now Pat. No. 10,500,013.

(60) Provisional application No. 62/216,206, filed on Sep. 9, 2015.

(51) Int. Cl.

| | |
|---|---|
| ***A61F 7/00*** | (2006.01) |
| *A61N 5/06* | (2006.01) |
| *A61N 5/10* | (2006.01) |
| *A61N 7/00* | (2006.01) |

(52) U.S. Cl.

CPC ............... *A61B 2017/00769* (2013.01); *A61B 2090/395* (2016.02); *A61N 5/062* (2013.01); *A61N 5/10* (2013.01); *A61N 7/00* (2013.01)

(56) References Cited

U.S. PATENT DOCUMENTS

| | | | | |
|---|---|---|---|---|
| 6,206,270 | B1 | 3/2001 | Huang | |
| 6,206,502 | B1 | 3/2001 | Kato et al. | |
| 6,997,923 | B2 | 2/2006 | Anderson et al. | |
| 8,224,064 | B1 | 7/2012 | Hassebrook et al. | |
| 8,663,162 | B2 | 3/2014 | Bunting et al. | |
| 8,920,379 | B2 | 12/2014 | Lee | |
| 10,500,013 | B2 | 12/2019 | Turner et al. | |
| 11,040,185 | B2 | 6/2021 | Johansson | |
| 2005/0148567 | A1 | 7/2005 | Kjellbotn et al. | |
| 2008/0009842 | A1 | 1/2008 | Manstein et al. | |
| 2008/0247637 | A1* | 10/2008 | Gildenberg ............ | A61B 34/70<br>901/41 |
| 2013/0041266 | A1* | 2/2013 | Rockrohr ............... | A61B 90/39<br>600/407 |
| 2013/0123746 | A1* | 5/2013 | Bunting ................. | A61B 50/13<br>604/116 |
| 2017/0065362 | A1 | 3/2017 | Turner et al. | |
| 2017/0065806 | A1 | 3/2017 | Niven et al. | |
| 2017/0065807 | A1 | 3/2017 | Niven et al. | |
| 2019/0046777 | A1 | 2/2019 | Knowlton | |
| 2019/0099199 | A1 | 4/2019 | Levinson et al. | |
| 2021/0244496 | A1 | 8/2021 | Niven et al. | |

OTHER PUBLICATIONS

Jamielyn Nye, Blue Stencilled Wall, iheartnaptime.net, Sep. 9, 2011.

Tim Van De Vall, Octagon Templates, timvandevall.com, 2014.

International Search Report; International Patent Application No. PCT/US2020/063831; Medline Industries, Inc.; Mailed Feb. 26, 2021.

Extended European Search Report; European Patent Application No. 20899868.2; Rejuvatek Medical Inc.; dated Apr. 13, 2023.

International Search Report and Written Opinion; International Patent Application No. PCT/US2024/015012; Rejuvatek Medical Inc.; dated Aug. 7, 2024.

* cited by examiner

TEMPLATE AND METHOD FOR REMOVING A TATTOO THROUGH PATTERNED TRANS-EPIDERMAL PIGMENT RELEASE

CROSS-REFERENCE TO RELATED APPLICATIONS

This application is a continuation-in-part of U.S. patent application Ser. No. 16/707,865 filed on Dec. 9, 2019 and entitled "Method for Removing a Tattoo Through Patterned Trans-Epidermal Pigment Release," which application is a continuation-in-part of U.S. patent application Ser. No. 15/261,670 filed on Sep. 9, 2016 entitled "Method for Removing a Tattoo Through Patterned Trans-Epidermal Pigment Release" and issued as U.S. Pat. No. 10,500,013 on Dec. 10, 2019, which claims the benefit of U.S. Provisional Patent Application Ser. No. 62/216,206 filed on Sep. 9, 2015 and entitled "Tattoo and Tattoo Removal Device and Method." The contents of each prior application are hereby incorporated by reference in their entirety.

BACKGROUND

Tattooing is the process of the introduction of colored inks into the dermis layer of skin to permanently color the skin. The process requires the controlled application of the colored inks to the dermis layer of a patient's skin, by repeatedly perforating the epidermis layer of skin with controlled punctures by needles coated in ink. Once punctured, the skin cells wipe the ink from the surface of the needles, which essentially stains these cells with the desired pigments.

Tattoos (as well as permanent make-up) can over time be less desirable for people due to poor design, social Stigma, or life changes (e.g., career or relationship changes, etc.). Tattoo removal can be difficult, costly, and painful. Improvements in tattoo removal are needed to better serve a large segment of customers with a less difficult, costly, and painful removal process.

SUMMARY

The subject matter of the present application has been developed in response to the present state of the art, and in particular, in response to the shortcomings of tattoo removal, that have not yet been fully solved by currently available techniques. Accordingly, the Subject matter of the present application has been developed to overcome at least Some of the shortcomings of prior art techniques.

Embodiments of a method for removing a tattoo through patterned trans-epidermal pigment release are described. In one embodiment, the method for removing a tattoo through patterned trans-epidermal pigment release includes determining first treatment area of skin of a patient through a primary template including primary apertures, marking the first treatment area of skin of the patient along borders of the primary apertures to outline a grid of primary tegulae, and delivering a tattoo removal fluid to the marked first exposed skin in a first treatment session. The method further includes determining a secondary treatment area through a secondary template including secondary apertures, marking the secondary treatment area along borders of the secondary apertures to outline a grid of secondary tegulae, and delivering a tattoo removal fluid to the secondary tegulae in a second treatment session. Other embodiments of a method for removing a tattoo through patterned trans epidermal pigment release are described.

Other aspects and advantages of embodiments of the present invention will become apparent from the following detailed description, taken in conjunction with the accompanying drawings illustrated by way of example of the principles of the invention.

The described features, structures, advantages, and/or characteristics of the subject matter of the present disclosure may be combined in any Suitable manner in one or more embodiments and/or implementations. In the following description, numerous specific details are provided to impart a thorough understanding of embodiments of the subject matter of the present disclosure. One skilled in the relevant art will recognize that the subject matter of the present disclosure may be practiced without one or more of the specific features, details, components, materials, and/or methods of a particular embodiment or implementation. In other instances, additional features and advantages may be recognized in certain embodiments and/or implementations that may not be present in all embodiments or implementations. Further, in Some instances, well-known structures, materials, or operations are not shown or described in detail to avoid obscuring aspects of the Subject matter of the present disclosure. The features and advantages of the subject matter of the present disclosure will become more fully apparent from the following description and appended claims, or may be learned by the practice of the subject matter as set forth hereinafter.

BRIEF DESCRIPTION OF THE DRAWINGS

In order that the advantages of the subject matter may be more readily understood, a more particular description of the subject matter briefly described above will be rendered by reference to specific embodiments that are illustrated in the appended drawings. Understanding that these drawings depict only typical embodiments of the subject matter and are not therefore to be considered to be limiting of its scope, the subject matter will be described and explained with additional specificity and detail through the use of the drawings.

Figure 1:
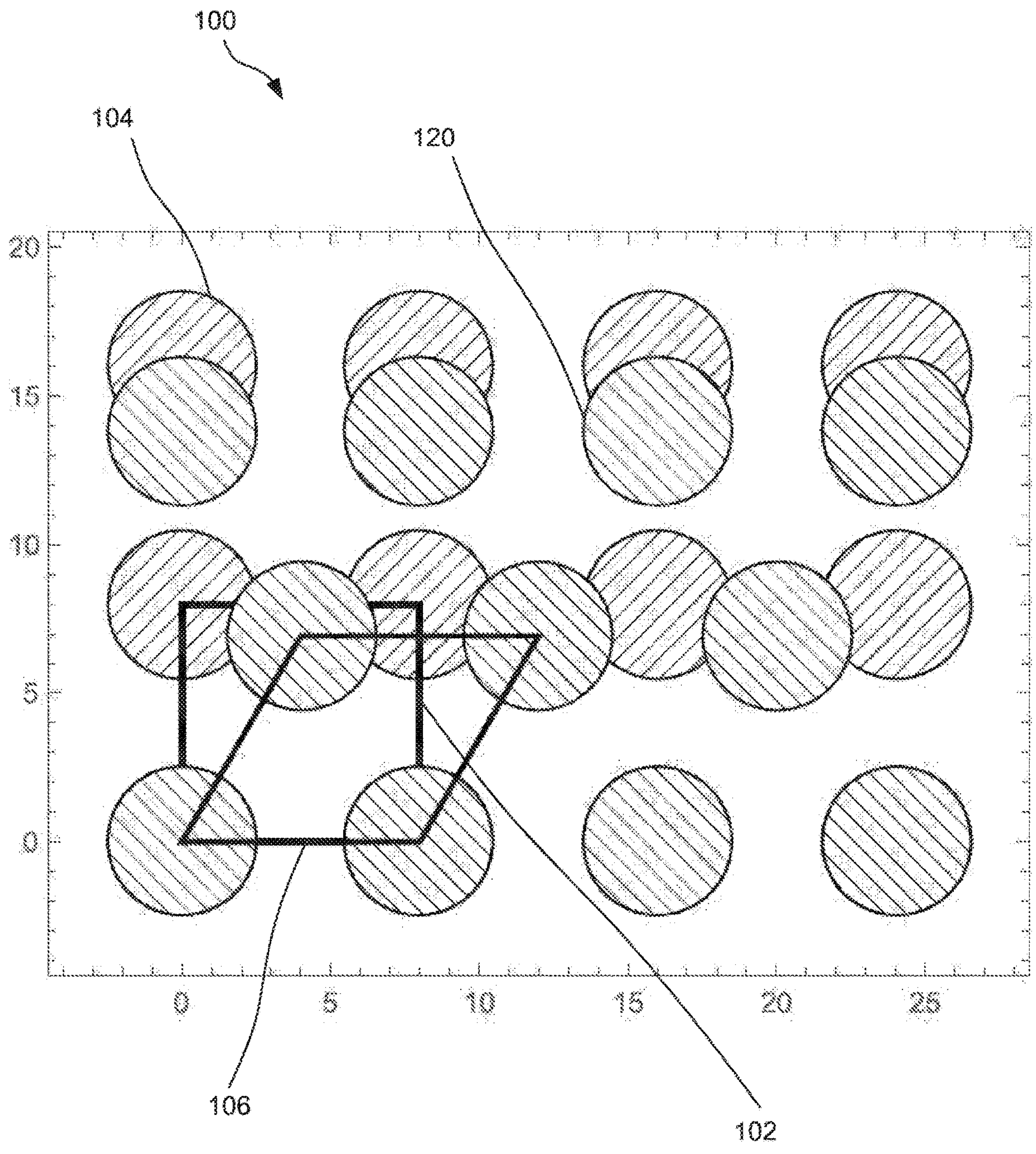
FIG. 1 depicts a template including a square pattern of circular apertures and an overlapping rhomboid pattern of circular apertures, according to one or more embodiments of the present disclosure.

It will be appreciated that the drawings are illustrative and not limiting of the scope of the invention which is defined by the appended claims. The embodiments shown accomplish various aspects and objects of the invention. It is appreciated that it is not possible to clearly show each element and aspect of the invention in a single figure, and as Such, multiple figures are presented to separately illustrate the various details of the invention in greater clarity. Similarly, not every embodiment need accomplish all advantages of the present invention.

While the disclosure is susceptible to various modifications and alternative forms, specific embodiments have been shown by way of example in the drawings and will be described in detail herein. However, it should be understood that the disclosure is not intended to be limited to the particular forms disclosed. Rather, the intention is to cover all modifications, equivalents and alternatives falling within the spirit and scope of the invention as defined by the appended claims.

Throughout the description, similar reference numbers may be used to identify similar elements.

DETAILED DESCRIPTION

It will be readily understood that the components of the embodiments as generally described herein and illustrated in the appended figures could be arranged and designed in a wide variety of different configurations. Thus, the following more detailed description of various embodiments, as represented in the figures, is not intended to limit the scope of the present disclosure, but is merely representative of various embodiments. While the various aspects of the embodiments are presented in drawings, the drawings are not necessarily drawn to scale unless specifically indicated.

The present invention may be embodied in other specific forms without departing from its spirit or essential characteristics. The described embodiments are to be considered in all respects only as illustrative and not restrictive. The scope of the invention is, therefore, indicated by the appended claims rather than by this detailed description. All changes which come within the meaning and range of equivalency of the claims are to be embraced within their Scope.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussions of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize, in light of the description herein, that the invention can be practiced without one or more of the specific features or advantages of a particular embodiment. In other instances, additional features and advantages may be recognized in certain embodiments that may not be present in all embodiments of the invention.

Reference throughout this specification to "one embodiment," "an embodiment," or similar language means that a particular feature, structure, or characteristic described in connection with the indicated embodiment is included in at least one embodiment of the present invention. Thus, the phrases "in one embodiment," "in an embodiment," and similar language throughout this specification may, but do not necessarily, all refer to the same embodiment.

While many embodiments are described herein, at least some of the described embodiments allow for the efficient removal of tattoos, permanent makeup, and other indelible mark or pigment on and under the skin. Some embodiments minimize retreatment overlap of tattooed skin. Some embodiment allow for efficient isolating of tattooed skin tiles (tegulae) for a final removal treatment. Some embodiments provide for front-loading removal of a tattoo in the first treatment. Some embodiments reduce the total number of treatment sessions. Some embodiments reduce the potential for scarring. Some embodiments are unaffected by skin movement and skin stretch.

While description herein refers primarily to tattoo removal, the apparatuses, systems, and methods described herein may be also be utilized for tattooing or other application of inks, etc., to the skin of a patient.

Trans-epidermal pigment release (TEPR) is a non-laser process for removing tattoo ink that employs partial thickness dermal injuries to initiate a beneficial healing response. These are Superficial injuries that penetrate into but not through the dermis. The beneficial response is the formation of an eschar or debris-scab of necrotized dermal tissue.

Tattoo ink is pushed out of the skin from below by the healing and regenerating epidermis and dermis.

U.S. Pat. No. 8,663,162 (Tattoo Removal System, 162 patent) describes a system for the controlled delivery of an eschar inducing material (EIM) via a pump to a handpiece with reciprocating needles, like those used in a tattoo machine. The combined mechanical injury (via the penetrating needles) and chemical injury (via the EIM) removes all epidermal cells, disrupts the dermal structure to a specified depth, and effectively initiates eschar formation. Subsequent healing completely removes the tattoo ink (independent of color and composition) from the injury site.

TEPR is most effective when injuries are localized to areas of skin bordered by uninjured skin. Embodiments described herein utilize templates to outline treatment areas of the skin and limit them to a specific size and shape that balances the need for bordering uninjured skin and a sufficient area to apply the TEPR process.

Keratinocytes are the cells responsible for the structure and barrier functionality of the cellular epidermis. A fresh wound (lacking a protective epidermis) is quickly covered by proliferating keratinocytes spreading (beneath the temporary scab) from non-necrotized, bordering tissue. The bordering uninjured skin is important to the healing process.

A wound becomes fully epithelialized when the thin layer of keratinocytes completely recovers the wound. This typically occurs within 2 to 3 weeks of the injury. After epithelialization is complete, the stratified layers of keratinocytes (found in mature epidermis) regenerate, while other cells in the dermis rebuild the underlying dermal matrix structure. Epidermal maturation requires months for completion, such as 8 to 12 weeks. The underlying dermal matrix is rapidly rebuilt with oriented fibers (characteristic of tough scar tissue), which are later remodeled over years into more pliable tissue. During dermal rebuilding, visible and hypertropic (raised) scars can form depending on the depth of the wound, genetic Susceptibilities, and aftercare (such as attempting to control trans-epidermal water loss and dermal stresses).

Keratinocytes proliferate to cover a fresh wound at rates determined by the natural growth and cell-cycle time governing mitosis (non-gametic cellular division). Thus, when the minimum linear or areal extent of the wound is large, epithelialization is delayed. This can result in fibrosis, hypertrophic scarring, and poor healing. The goal of TEPR is to produce wounds in spatial patterns that are conducive to both healing and eschar formation. When wounds are too Small, ink-agglomerating eschars will be limited or will not form. When wounds are too large, the skin will be damaged and scarring will prevail. Embodiments described herein utilize templates (see e.g., FIGS. 4, 5, and 7) to mark potential treatment areas to optimize the size and shape of wounds.

Unlike laser treatment, TEPR removes all tattoo ink at the treatment site in a single session. Because TEPR treatment always occurs locally at sites bordered by untouched skin, tattoos must be removed piecemeal. A series of treatment sessions, each separated by inter-session healing periods (lasting approximately from 8 to 12 weeks), are utilized to completely remove a full-area tattoo, in which the entirety or greater majority of the skin is tattooed. Modern multiple-color tattoos are typically full-area tattoos.

Embodiments of an advanced TEPR series accomplish various goals to optimize treatment during tattoo removal. Embodiments minimize overlapping retreatment areas to minimize dermal sensitization, inflammatory reaction, and the potential for visible scarring. Embodiments deal effectively with the vagaries of manual treatment by, for example, automatically compensating for skin movement and stretch. Finally, embodiments allow for completion of the removal process in a minimum number of treatment sessions.

Embodiments of an advanced TEPR process simultaneously accomplish Some or all of these goals. The fundamental idea is the divide the tattooed surface into skin tiles that completely cover the skin with minimal overlap and remove evenly spaced skin tiles (tegulae) in a series of treatment sessions. To accomplish this, treatment sites in the shape of only the circular disks (as disclosed by the 162 patent) cannot be used for all treatment sessions. The treatment sites of skin tiles may be called tegulae (singular, tegula, and adjective form, tegular). The etymological derivation of the name literally means “skin tile', being taken from the ancient Roman “imbrex and tegulae' roof tiling system and skin as the “tegument of the body.

In contrast to some methods with overlapping treatment sites, embodiments of an advanced TEPR process break up a surface into theoretical tegulae that fully cover the Surface without overlap. Some tegulae in a series may be circular, but not all. Tegulae may be round, square, hexagonal, triangular, polygonal, arbitrarily shaped, curvilinear, or a combination of polygonal and curvilinear. A complete tiling series may contain just one kind of tegula (see e.g., FIGS. 10 and 11) or many different shaped and sized tegulae 600 (see e.g., FIG. 6) in combination.

Each session in a series treats some tegulae and leaves others intact. For any particular session, treated or “excised tegulae are called extegs, while intact or “integral tegulae are called integs. Tegulae that are extegs in one session are integs in other sessions, and vice versa.

To prevent leaving bordering halos of ink, in some embodiments, pragmatic extegs may be slightly larger than their theoretical counterparts; in other words, pragmatic excised tegulae are minimally overlapping.

Referring to shortcomings of traditional treatment patterns and process, FIG. 1 depicts a template 100 including a square pattern 102 of circular apertures 104 (represented with a hatch from upper right to lower left) and an overlapping rhomboid pattern 106 of circular apertures 120 (represented with a hatch from upper left to lower right). The 162 patent describes templates for applying a TEPR pattern to tattooed skin (the 162 patent, FIG. 8, and claims 1, 7, and 8). TEPR treatment sites (called “dots” in the 162 patent) are disk-shaped areas marked on the skin through template holes called apertures. Circular aperture diameters (d) may range from 3 to 6 mm, with 5 mm being preferable. The separation (h) between template apertures may range from 2 to 5 mm, with 3 mm being preferable. FIG. 1 depicts a scale on the X-axis and y-axis in millimeters.

The 162 patent does not specify any particular pattern or aperture arrangement, but merely describes a template with “constant diameter and “uniformly spaced circular apertures.” This description admits a continuum of regular templates. All place circular apertures on grid line intersections, or equivalently, at the vertices of rhomboidal unit cells that define the grid (see e.g., FIG. 1). A rhomboidal unit cell has the shape of a general rhombus or equilateral parallelogram. Equilateral unit cells ensure uniform aperture spacing.

With apertures aligned in a square grid, the generalized rhomboidal unit cell becomes a square (with side s-d-h). When adjacent rows of apertures are horizontally shifted, square unit cells become skew rhomboidal or diamond shaped (see e.g., FIG. 4). This shifting decreases the row spacing, compacts the arrangement, and favorably increases the aperture-to-unit-cell area ratio. Because each rhomboidal unit cell contains exactly one quadrisected aperture, this area ratio exactly equals the fractional coverage of one pattern application. For the same aperture diameter and spacing, a more compact arrangement will yield a larger factional coverage, which means that more of the tattoo can be removed in a single treatment session.

The least compact regular arrangement is the square grid. The most compact arrangement occurs with rows shifted so their grid points lie exactly between adjacent row grid points (see e.g., FIG. 4). This produces a rhomboidal unit cell composed of two equilateral triangles, which defines the grid. It is sometimes referred to as a hexagonal lattice, so named because each grid point is equidistant from six neighboring grid points.

Figure 2:
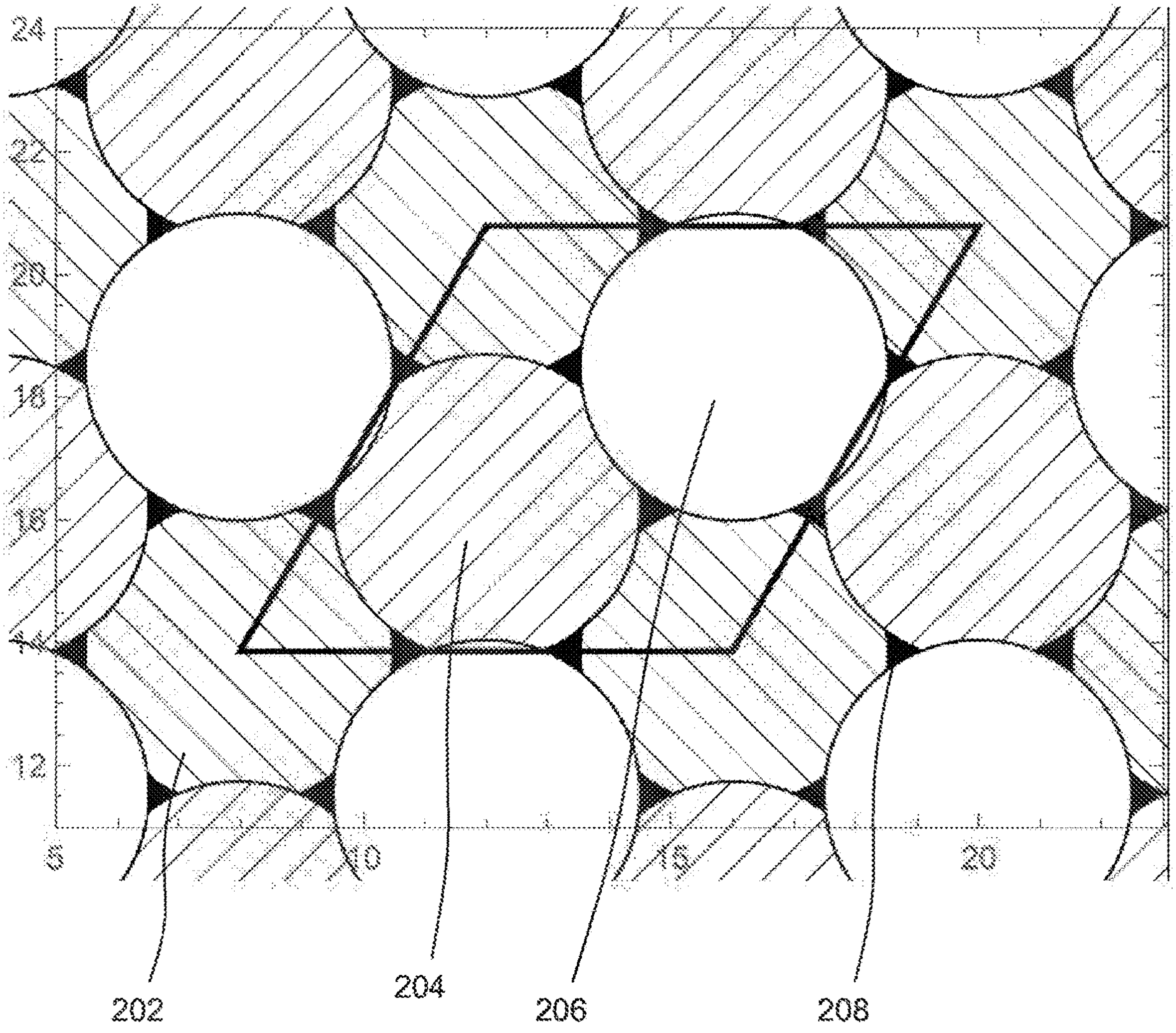
FIG. 2 depicts a treatment pattern resulting from three treatments utilizing optimally placed templates of a rhomboid pattern of circular apertures, according to one or more embodiments of the present disclosure.
Figure 8:
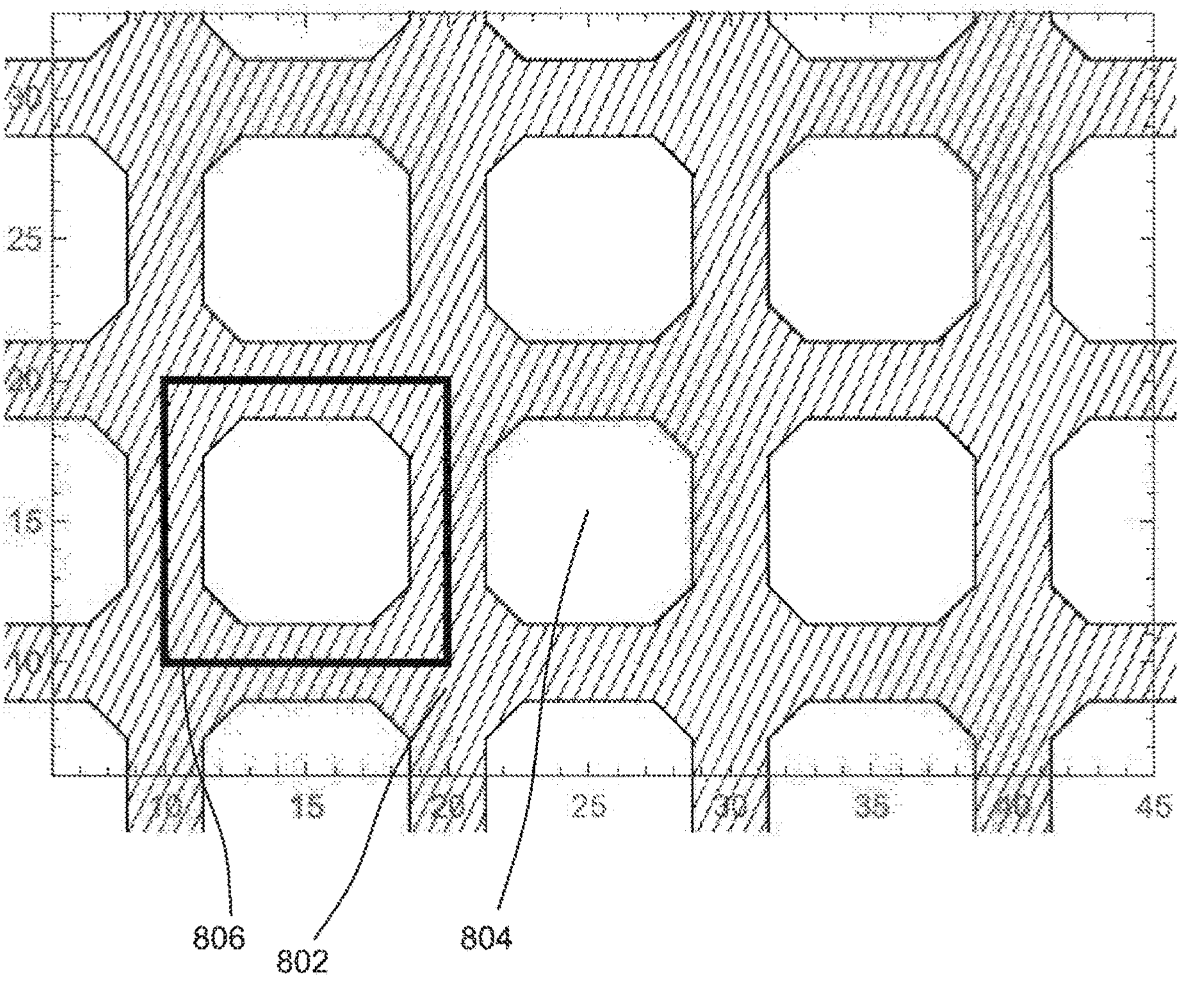
FIG. 8 depicts a treatment pattern resulting from a square pattern of octagonal apertures, according to one or more embodiments of the present disclosure.

FIG. 8 of the 162 patent shows a template with circular apertures on a hexagonal lattice. Other drawings (such as FIGS. 9-11 of the 162 patent) show how this rhomboid pattern can be shifted and reapplied to fully cover the area in a series of three treatment sessions (see also e.g., FIG. 2 of the current application showing primary tegulae 202 for the first treatment session, secondary tegulae 204 for the second treatment, and tertiary tegulae 206 for the third treatment). FIG. 2 further depicts a scale on the x-axis and y-axis in millimeters.

A similar series of treatment sessions is required to fully cover an area with a square grid pattern, but in this case four sessions are required. Treatment sessions in a series may be named by order: primary, secondary, tertiary, qua ternary, quinary, etc.

Although not explicit, the square grid pattern is also implied in the 162 patent disclosure, where a series of four treatment sessions is deemed necessary for full removal: (162 line 2:19) "approximately, four such treatment session are generally required, and then (162 line 2:37) "an average number of treatments is at least four to eight' depending on tattoo size. Because large tattoos are typically divided into two treatment areas, the latter implies four sessions per treated area, as would be required by a Square grid pattern.

Years of experience with the classic pattern (i.e., 5 mm diameter disks, centered on hexagonal lattice points and spaced 8 mm apart) have shown that the template is necessary and effective in providing the proper pattern spacing. Further, when a template is not used during the primary treatment session, Subsequent sessions in the removal series are technically more difficult. In addition to the three required coverings sessions for a hexagonal lattice pattern, one to three extra sessions are always required to completely remove the remnants of a full-area tattoo. As a consequence, skin stretching, subsequent pattern applications may be distorted with respect to those laid out in earlier treatment.

Yet, even if skin did not stretch and the theoretical pattern was applied perfectly each time, several extra treatment sessions would always be necessary because of a design defect not recognized by the inventors. The 162 patent calls for a series of treatments with the same pattern shifted to cover untreated skin left intact by prior treatments. Yet, even when this is done perfectly, the preferred design leaves uncover defects 208 (see e.g., FIG. 2), where the skin is not TEPR-treated and where the tattoo is not removed even after three treatment sessions. To remove these uncover defects 208 requires several extra treatment sessions.

Although small, these triangle-shaped tattoo remnants (e.g., 208) are numerous. For a rhomboid pattern there are six times as many defects as pattern apertures. Because these defects are uniformly distributed, they require multiple treatments for removal.

Eschar formation and pigment release may be inhibited when treatment disks are too small. Thus, a strategy for removing Small defects is to group them together. Yet, because they are uniformly distributed, only two defects fit within a standard 5 mm treatment disk. The six defects (per pattern aperture) may thus require as many three extra treatments to completely remove the tattoo remnants. This doubles the total number of treatments required. The three extra treatments are also more technically difficult that the original three, because the same patches of skin must be retreated.

Human skin never regenerates its virgin state. Scar tissue naturally forms as injuries heal. Tattooing and tattoo removal generate scar tissue, which when significant or hypertrophic appears as visible Scars. One great advantage of TEPR treatment over laser removal is that a patch of tattooed skin need only be treated once. (The average laser removal—one treatment followed by nine retreatments—substantially destroys the pliable dermal substructure.) Extra TEPR retreatments diminish this advantage. Additionally, skin becomes sensitized to TEPR treatment and to the EIM used. As a consequence, retreated skin reacts stronger and generates more scar tissue. In a perfect TEPR process, retreatment would be avoided.

To better understand the nature of the design defect, it is useful to plot theoretical uncover 306 and overlap 308 functions (see e.g., FIG. 3) with respect to the aperture diameter-to-spacing ratio (d/s) 302. Uncover 306 is the area fraction 304 remaining untreated after the full TEPR series is complete. For rhomboid patterns of circular apertures, a full series consists of 3 treatment sessions. For square grid patterns, a full series consists of 4 treatment sessions. Overlap 308 is the skin area fraction 304 retreated multiple times. An optimal strategy for effective tattoo removal minimizes overlap 308 while Zeroing uncovered area.

Figure 3:
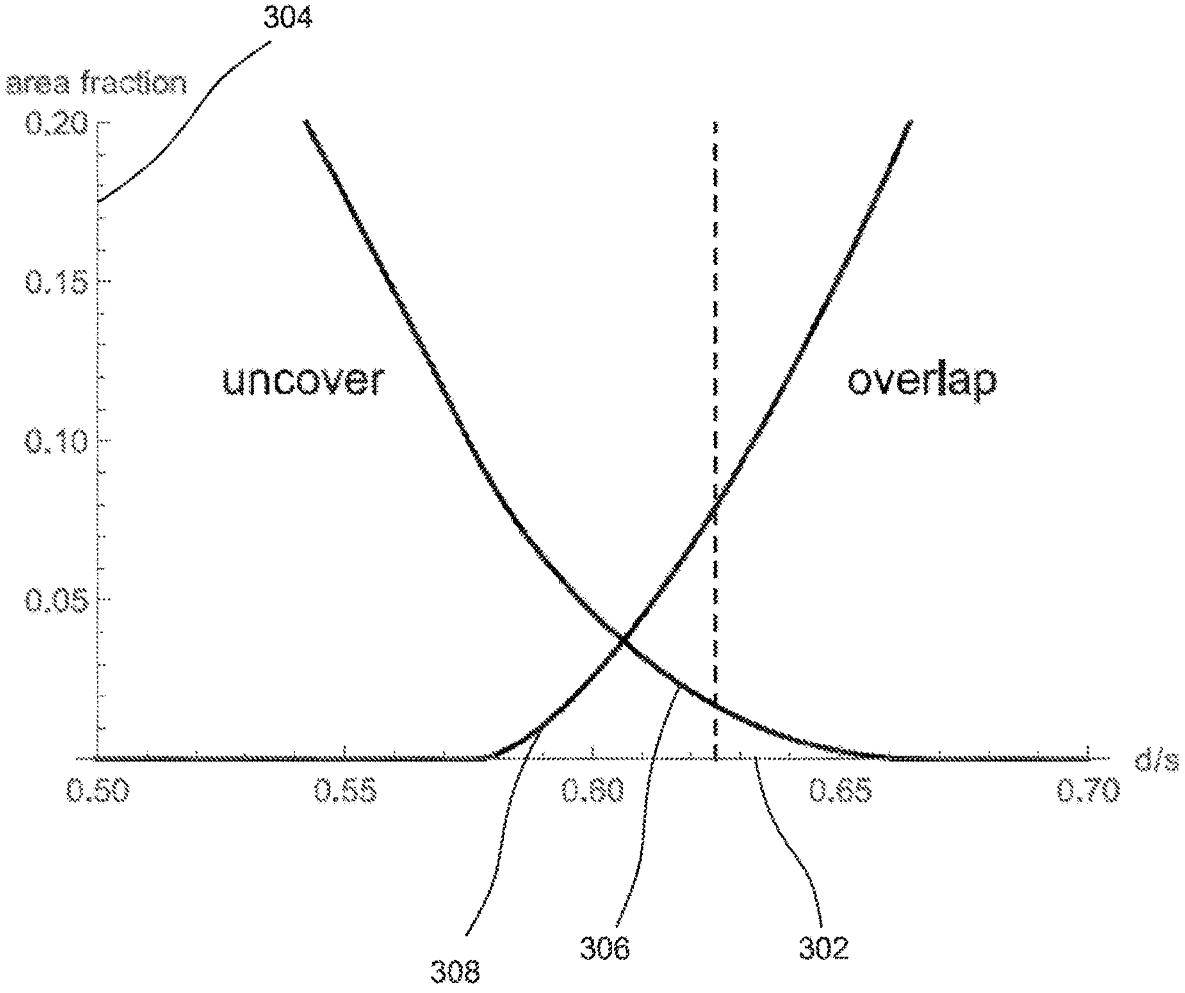
FIG. 3 depicts a graphical representation of a diameter to spacing ratio depicting the amount of uncovered skin area and the amount of overlap skin versus the diameter to spacing ratio of apertures of a template, according to one or more embodiments of the present disclosure.

FIG. 3 shows that, for all rhomboid patterns of circular apertures, uncover 306 cannot the Zeroed without incurring significant overlap 308. Uncover 306 and overlap 308 functions for all square patterns are similar but worse: much more overlap is required to Zero out the uncover area.

The diameter-to-spacing ratio (d/s) 302 is a crucial parameter that determines the uncover 306 and overlap 308 of the treatment series for a particular pattern. For rhomboid patterns of circular apertures, uncover is Zeroed only when d/s-2/3. This was not recognized in the 162 patent, wherein the possibility of uncover defects was not even mentioned.

The 162 template drawing (162 FIG. 8) and treatment series snippets (162 FIGS. 9, 10 and 11) were not drawn to scale. As shown, the template diameter-to-spacing ratio is close to one-half (d/ss0.5), which is significantly smaller than the preferred design (162 column 8, lines 27-30), where d/s=5/8. In contrast, the treatment series Snippets used to demonstrate complete coverage (with d/ss0.7) exceed the preferred design.

Given the design range provided by the patent (162 claim 1) with 3sds6 and 2shs5 mm, the criterion to Zero the uncover can be satisfied for rhomboid patterns of circular apertures with 6 mm apertures spaced less than 3 mm apart, but this was not recognized by the 162 patent.

The minimal requirement for any useful TEPR series is complete coverage of the tattooed skin. (This assumes the most difficult case, which is the removal of a full-area tattoo. Obviously, when removing partial-area tattoos, or when selectively modifying tattoos in preparation for a cover-up tattoo, this requirement can be relaxed.)

Figure 4:
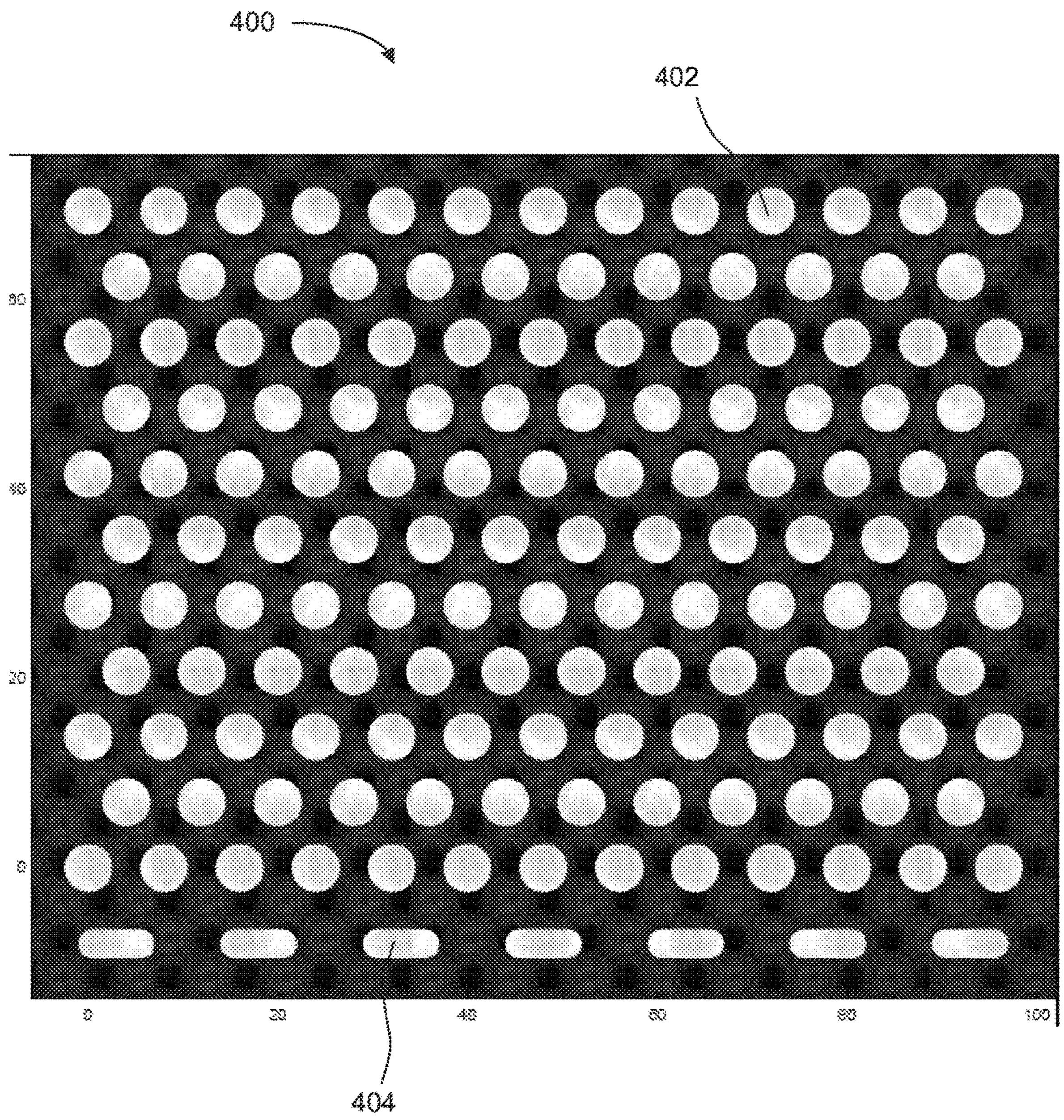
FIG. 4 depicts a template with a rhomboid pattern of circular apertures and one row of elongated apertures, according to one or more embodiments of the present disclosure.
Figure 5:
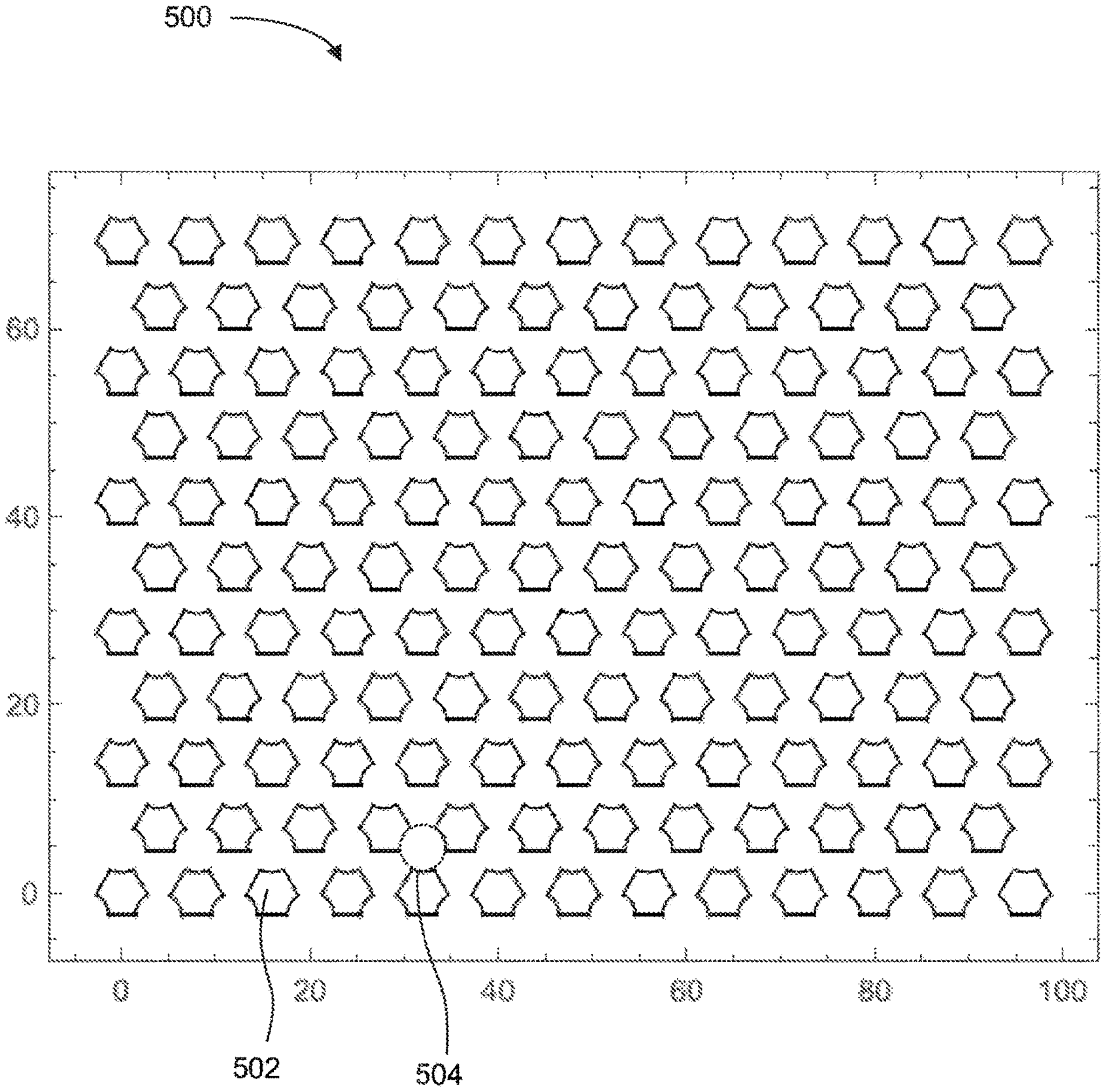
FIG. 5 depicts a template with a rhomboid pattern of non-circular and non-polygonal apertures, according to one or more embodiments of the present disclosure.
Figure 6:
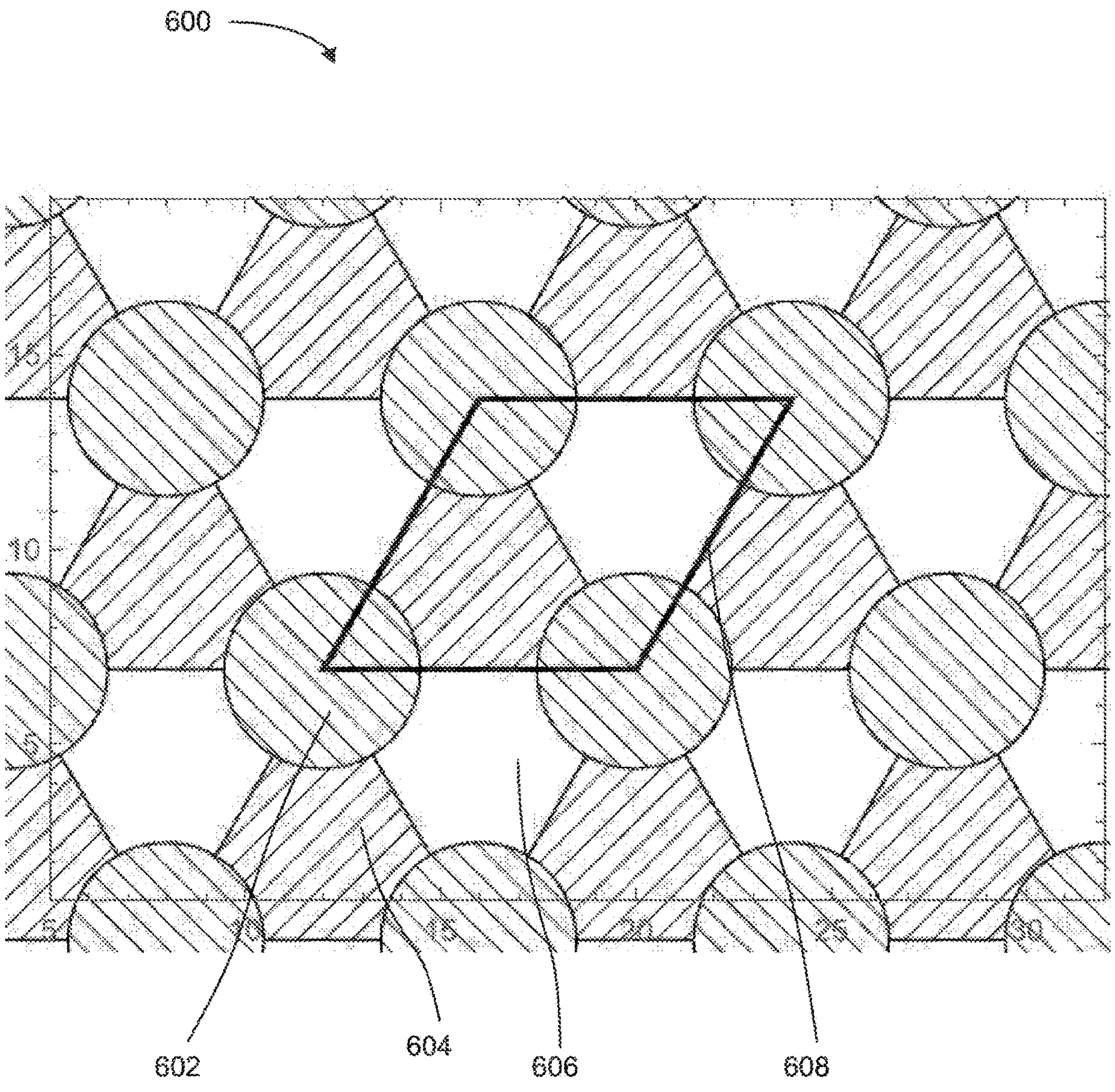
FIG. 6 depicts a treatment pattern resulting from a first treatment utilizing a primary template with a rhomboid pattern of circular apertures and a second treatment using a secondary template with a rhomboid pattern of non-circular and non-polygonal apertures, according to one or more embodiments of the present disclosure.

In embodiments of an advanced TEPR process, referring to FIGS. 4-6, a first treatment session may include the use of template 400 with a rhomboid pattern (see e.g., 608 of FIG. 6) of circular apertures 402. A second treatment session may include the use of template 500 with a rhomboid pattern of a non-circular and non-polygonal apertures 502. The array of non-circular and non-polygonal apertures 502 would align with the circular apertures 402 as shown by dotted line circle 504 in FIG. 5. A third treatment session would remove the remaining isolated tegulae marked by remnant tattoo ink. The template 400 may be a sheet of material with a plurality of apertures spaced in a repeating pattern. In some embodiments, the sheet of material is configured to be flexible to conform to a non-flat surface of skin of a patient. In some embodiments, the sheet of material is configured to be flexible while not stretching. That is, the distance between apertures does not increase through stretching in a transverse direction between the apertures.

In one embodiment, the circular apertures 402 are 5 mm diameter disks, spaced 8 mm apart. The circular apertures 402 combine to cover approximately 35 percent of a unit cell (represented by rhombus 608 in FIG. 6). The remaining 65 percent is split evenly between secondary tegulae 604 and tertiary tegulae 606. These extegs are triangulations of the hexagonal lattice, minus the primary disks. That is, the secondary tegulae 604 (i.e., the treatment area for the second treatment session) and tertiary tegulae 606 (i.e., the treatment area for the third treatment session) are combinations of a polygonal shape (triangle) and a curvilinear shape (excised segment of a circle). The triangle is formed with vertices at the center of the circular apertures and the corners of the triangle are removed as segment of the circular apertures. The shape formed is the non-circular and non-polygonal apertures 502 depicted in FIG. 5.

How extegs are excised is the differentiator between overlapping and an advanced TEPR process. The primary treatment is identical for both: utilizing the template 400 to determine a first or primary treatment area of skin. The template 400 and apertures 402 guide a skin marking pen as exposed skin of a patient (through the template 400) is marked along the borders of the circular apertures 402. The skin could be marked by any of a number of apparatuses in any number of ways including, for example, spray on ink from an airbrush which may be driven with canned air or by an external pressurized air system. A handpiece (or actuating device and needle cartridge) (supplied with a controlled flow of EIM) is then used to score each marked primary tegula (see e.g., 602 in FIG. 6). This process gray lines the circular primary tegulae 602. The skin is then cleaned removing all the markings except the gray lined primary tegulae 602. The handpiece is then used to excise each primary tegulae 602, removing all epidermal cells until the densely inked reticular dermis is uncovered. The excision also sharpens and defines tegular boundaries and disrupts the interior dermal structure, both mechanically and chemically.

In an advanced TEPR process, secondary and tertiary treatments differ markedly from the primary treatment, especially during the all-important excision pass. Secondary tegulae 604 are marked with the template 500 shown in FIG. 5. The broken circles (represented by dotted line circle 504) in the template 500 are aligned with the primary tegulae 602, which now (after the healing process) markedly stand out as healed fresh skin, polka-dotting the inked tattoo. The template 500 may be readjusted as necessary so that broken circles are always aligned near the primary tegulae 602 being marked.

Scoring proceeds in a manner similar to what is described above. After the skin is cleaned, excision proceeds as usual except when sharpening exteg borders. These borders are defined be the primary tegular disks (the healed polka dots) and theoretical lines connecting their centers. Although unmarked, borders are easily visualized as mental constructions connecting the healed polka dots. Care may be taken to TEPR-treat all inked skin within these borders. It is this important procedural difference that eliminates all uncover defects (see e.g., 208 of FIG. 2) and compensates for skin movement and stretch.

In effect, the healed primary tegulae 602 act as permanent alignment markers that directly define the exteg pattern of the secondary tegulae 604. Even so, the secondary tegulae 604 cannot be easily identified and marked without the secondary template 500. Attempting to mark them by eye (without a guide), results in mistakenly marking an integ (i.e., the tertiary tegulae 606) as an exteg for the second treatment session. Every mistake puts two extegs together, which would result in removing bordering tertiary tegula 606 and secondary tegula 604. The size may prevent their removal. Such mistakes may force an extra retreatment session.

After the primary and secondary treatments, all the remaining tattoo ink is sequestered within the tertiary tegulae 606. The third treatment does not require any template whatsoever as the tertiary tegulae 606 are isolated ink. One simply treats the remaining ink. That is, the now healed primary tegulae 602 and the now healed secondary tegulae 604 form isolated ink patterns (i.e., the tertiary tegulae 606). FIG. 6 depicts a grid of primary tegulae 602 (i.e., the grid of right hatched circles), a grid of secondary tegulae 604 (i.e., the grid of left hatch non-circular and non-polygonal shapes), and a grid of tertiary tegulae 606 (i.e., the grid of non-circular and non-polygonal shapes that are not hatched. As depicted, each of the primary tegulae 602 border three secondary tegulae 604 and three tertiary tegulae 606, each of the secondary tegulae 604 border three primary tegulae 602 and three tertiary tegulae 606, and finally each of the tertiary tegulae 606 border three primary tegulae 602 and three secondary tegulae 604. The secondary tegulae 604 and the tertiary tegulae 606 are the same shape. The process described in conjunction with FIG. 6 results in a tattoo removal requiring only three treatment session.

Because TEPR locally treats skin in areas bordered by intact skin, there are fundamental constraints limiting the possible patterns and series useful in tattoo removal. All TEPR tiling series can be categorized as skin-bridge series (see e.g. FIG. 6), skin-island series (see e.g., FIGS. 8 and 9), or point-connected series (see e.g., FIGS. 10 and 11). There are no other possibilities, except for lateral and nested combinations of these three.

In skin-bridge series, extegs (i.e., the tegulae corresponding to the particular treatment session) are disconnected from each other, being isolated by an enclosing network of integs (the other two tegulae not corresponding to the particular treatment session). Integs form the untreated skin bridges that Surround and isolate extegs from one another. For example, the secondary tegulae 604 and the tertiary tegulae 606 together form untreated skin bridges (Surrounding the primary tegulae 602) during the first treatment session. The primary tegulae 602 and the tertiary tegulae 606 together form untreated skin bridges (surrounding the secondary tegulae 604) during the second treatment session. And finally, the primary tegulae 602 and the secondary tegulae 604 together form untreated skin bridges (surrounding the tertiary tegulae 606) during the third treatment session.

FIG. 6 illustrates a useful skin-bridge tiling series. (Although not a tiling series, the classic overlapping pattern defined by US patent 162 and illustrated by FIG. 1 also forms a skin-bridge series.) The minimum number of treatment sessions required to complete a skin-bridge tiling series is three sessions.

One exception to this rule for skin-bridging series concerns removal areas where individual tegulae can be elongated to span the entire wide of the area. In this case, the removal area can be covered in two treatments with a striped tiling pattern.

Striped skin-bridge series are a subset of skin bridge series processes. A striped pattern, where equal height tegulae span the entire removal area can tile an elongated area in two sessions. The template used to layout the primary pattern is a series of rectangular slots or elongated elliptical slots (see e.g., elongated apertures 404 in FIG. 4) in a linear pattern. FIG. 4 further depicts a scale on the X-axis and y-axis in millimeters.

Striped patterns are particularly advantageous when treating linework. In this case, tegulae are narrowed and elongated (tegula area remaining about the same) to efficiently cover a narrow line in two treatments. The resulting, linearly elongated, striped pattern is called a linear pattern. A linear template of two or more elongated apertures 404 can be used to lay out a striped pattern along straight and/or curvilinear lines. An example is illustrated as the bottom row of the template shown in FIG. 4.

A particular advantage of striped patterns used to cover large areas is the possibility of aligning the stripes with the natural structural orientation of the underlying dermis. Oriented incisions are routinely used in plastic Surgery to promote healing and minimize scarring. Striped orientations (parallel to the flowing pattern of Langer lines) can be used to promote healing and minimize scarring in tattoo removal.

Figure 9:
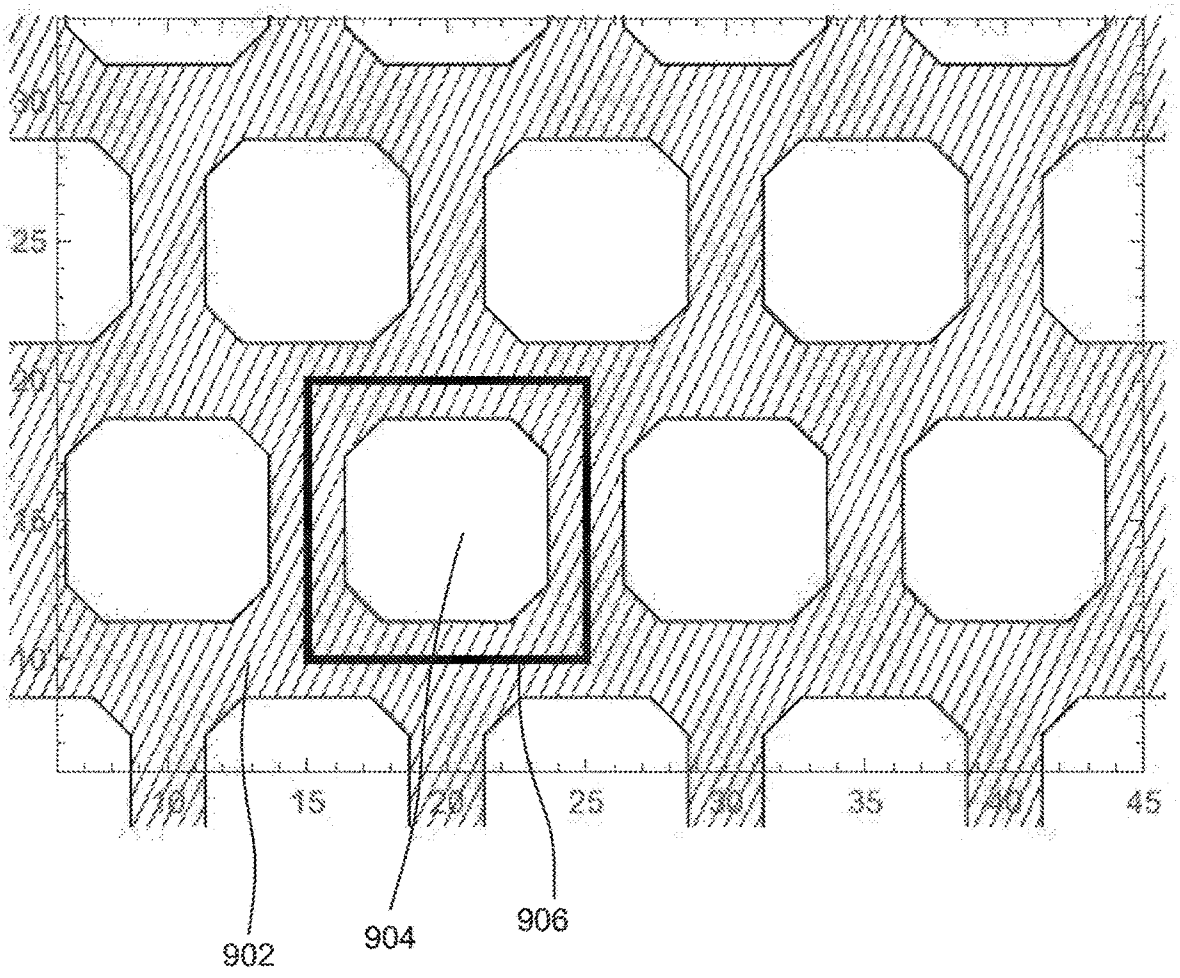
FIG. 9 depicts a template with a rhomboid pattern of octagonal apertures, according to one or more embodiments of the present disclosure.

In skin-island series, extegs are connected in a lattice network that isolates integs as secondary tegulae 804. FIGS. 8 and 9 illustrate useful skin-island tiling series. To better understand and alleviate the dermal stresses that develop during healing, an exteg net is conceptually decom posed into linear (or curvilinear) lanes and interconnecting nodes. Skin-island series are a kind of reverse or negative to skin-bridge series. In both, extegs are bordered by intact skin, whether in the form of skin-bridges or skin-islands. Skin-island series are interesting because some can be completed in the minimum possible number of treatment sessions, which is two sessions.

Figure 7:
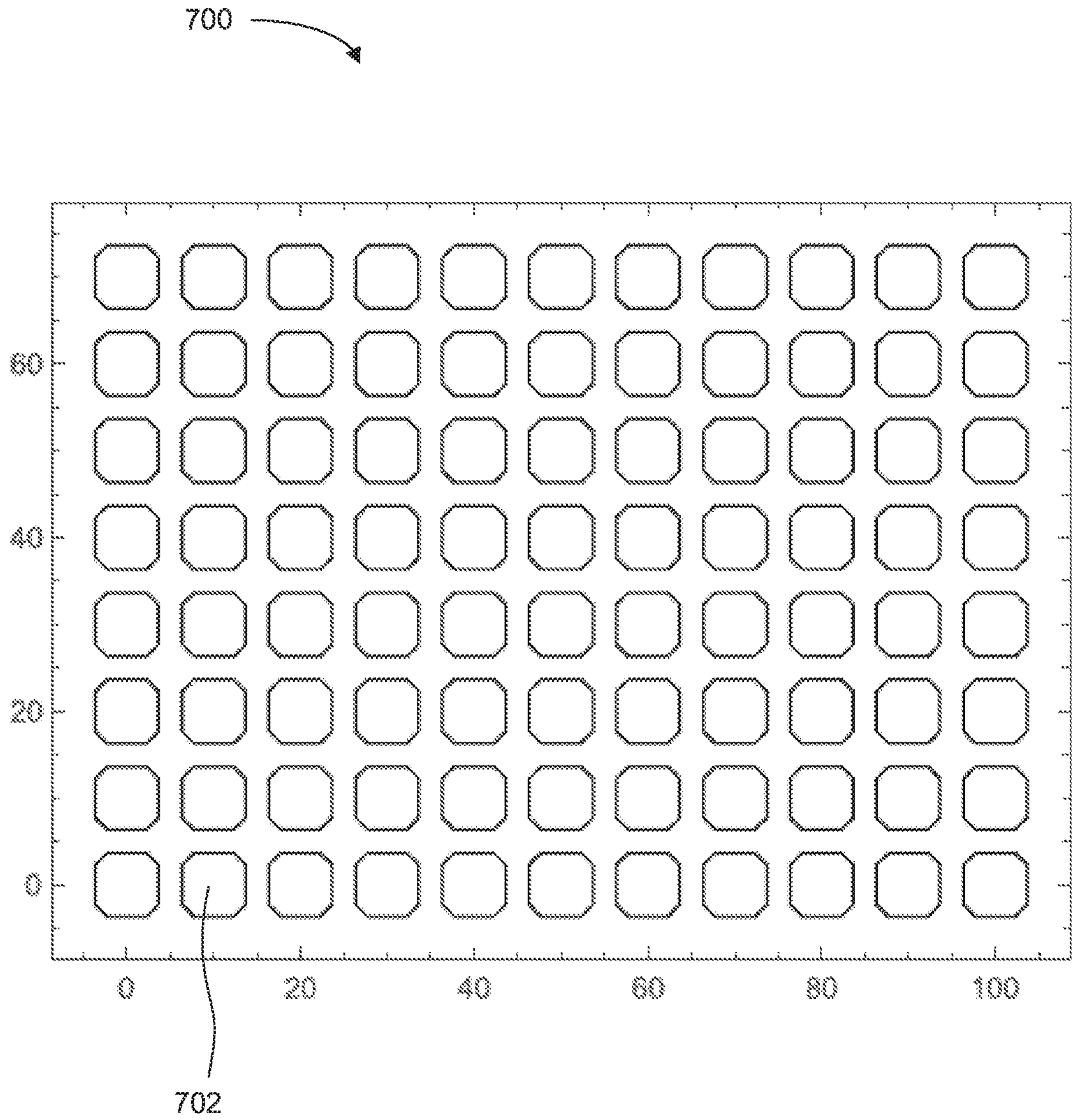
FIG. 7 depicts a template with a square pattern of octagonal apertures, according to one or more embodiments of the present disclosure, according to one or more embodiments of the present disclosure.

Referring to FIG. 7, the template 700 with a square pattern of octagonal shaped apertures 702 is utilized as a negative template (rather than positive) in that it directly marks the integs and not the extegs. The primarily treated or excised area (i.e., the primary lattice tegulae 802) is depicted as hatched and is treated during the first treatment session while leaving the secondary tegulae 804 as integs.

The fundamental idea underlying all skin-island series is to isolate easily removable integs (the skin islands, see e.g., secondary tegulae 804 in FIG. 8 or secondary tegulae 904 in FIG. 9) by completely surrounding them with a lattice network of extegs (represented by hatched area 802) which form a primary lattice tegulae 802. Both secondary tegulae and the primary lattice tegulae (e.g., 802 and 902) should be shaped so they can be readily TEPR-treated. Both embodiments depicted in FIGS. 8 and 9 satisfy these basic requirements.

Skin-islands series are interesting because they can completely remove a tattoo in one less treatment than the best skin-bridge series. Only two treatments are required to complete a skin island series. Thus, both primary and secondary treatments should excise approximately equal areas of skin. The two series illustrated (FIGS. 8 and 9), evenly divide the unit cell area 806, 906.

The primary lattice tegulae (e.g., 802 and 902) is conceptually composed of straight lanes and interconnecting nodes. One problem with long linear TEPR excisions (as depicted in FIG. 8) is the potential for generating long linear Scars. Uniform cross stresses (contractive tensions across the wound) develop as long linear tegulae heal. In contrast, more compact wounds typically do not produce visible Scars. Linear Scarring is avoided because the stresses developed during healing are more isotropic.

A couple techniques can be used to break up the long linear regions of cross stress. FIG. 8 illustrates an approach. The enlarged and near radially-symmetric nodes produce near isotropic stresses during healing. These break up the cross stresses in the extended lanes. As a result, the potential for long linear scarring is reduced. FIG. 9 illustrates an additional technique of offsetting lanes and thereby breaking up long linear features in one direction.

Lattice tegulae (e.g., 802 and 902) are designed to be easily constructed. Parallel lines are excised in perpendicular directions to form a square grid. Integ corners are next clipped to form the enlarged nodes. Clipping is also valuable in making the octagonal integs more circular and thereby easier to excise in the second treatment session.

Extended exteg lanes can be marked with a template consisting of parallel linear apertures, like those used to layout Striped patterns. One set is marked, the template is rotated a quarter turn, and then the second set is marked. Alternately, a negative template can be used to outline the pattern (see e.g., FIG. 7). It is negative template in the sense that integs rather than extegs are marked at the boundary of the octagonal apertures 702.

Secondary treatments do not require templates, because the remaining tattoo ink has already been sequestered within easy to remove octagons. The pattern is the ink itself.

One of the major accomplishments of advanced tiling series is minimization of the total number of treatment sessions required for full tattoo removal. This is important because the healing response of Subsequent treatment sessions is reduced with each treatment. Client pressures to remove the unwanted tattoo rapidly, typically cause removal sessions to be scheduled with the minimum intersession healing period (typically 8 to 12 weeks). Although the epidermis has reformed, the skin is still maturing and remodeling and will do so for many months and even years. As a consequence, Subsequent treatments (especially with overlapping patterns) inadvertently (or purposely) retreat newly healed skin with a Subsequent loss in the healing response.

Because the first treatment always heals best, more skin should be treated first. Thus, an advanced series will purposely decrease the fractional area treated with each session. The table below gives possible removal sequences for both 3-session and 2-session series. In every case, the total area treated exceeds unity because of minimal overlaps that are pragmatically required.

All the tiling patterns discussed (including those discussed in conjunction with FIGS. 4-9) can be adjusted to optimize the amount of skin treated in the first and subsequent sessions.

| Tiling series | Area fraction removed | Overlap fraction |
|---|---|---|
| 3-session series | 0.50 + 0.35 + 0.25 | 0.10 |
| 2-session series | 0.60 + 0.45 | 0.05 |

Figure 10:
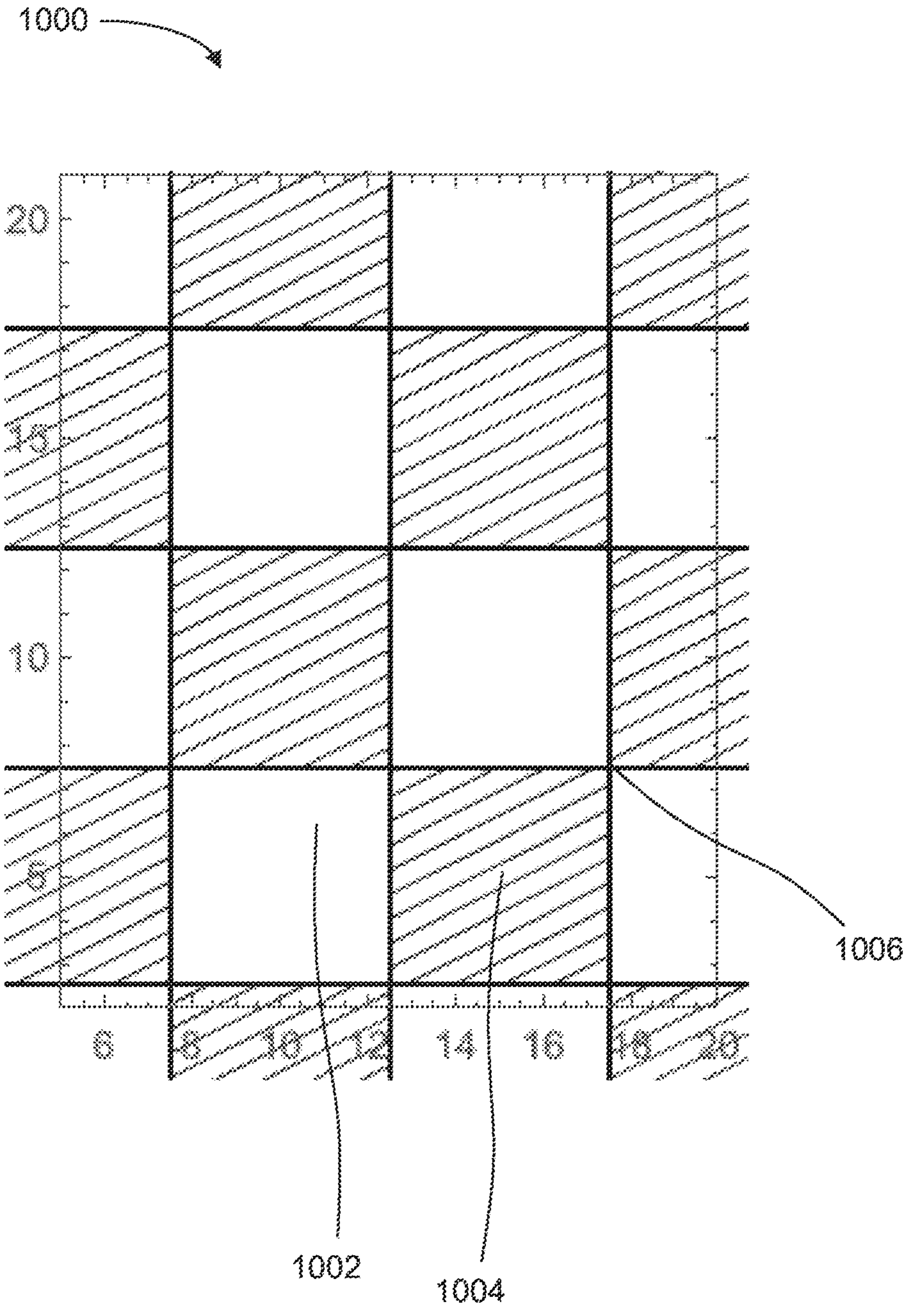
FIG. 10 depicts a point connected treatment pattern with square tegulae, according to one or more embodiments of the present disclosure.
Figure 11:
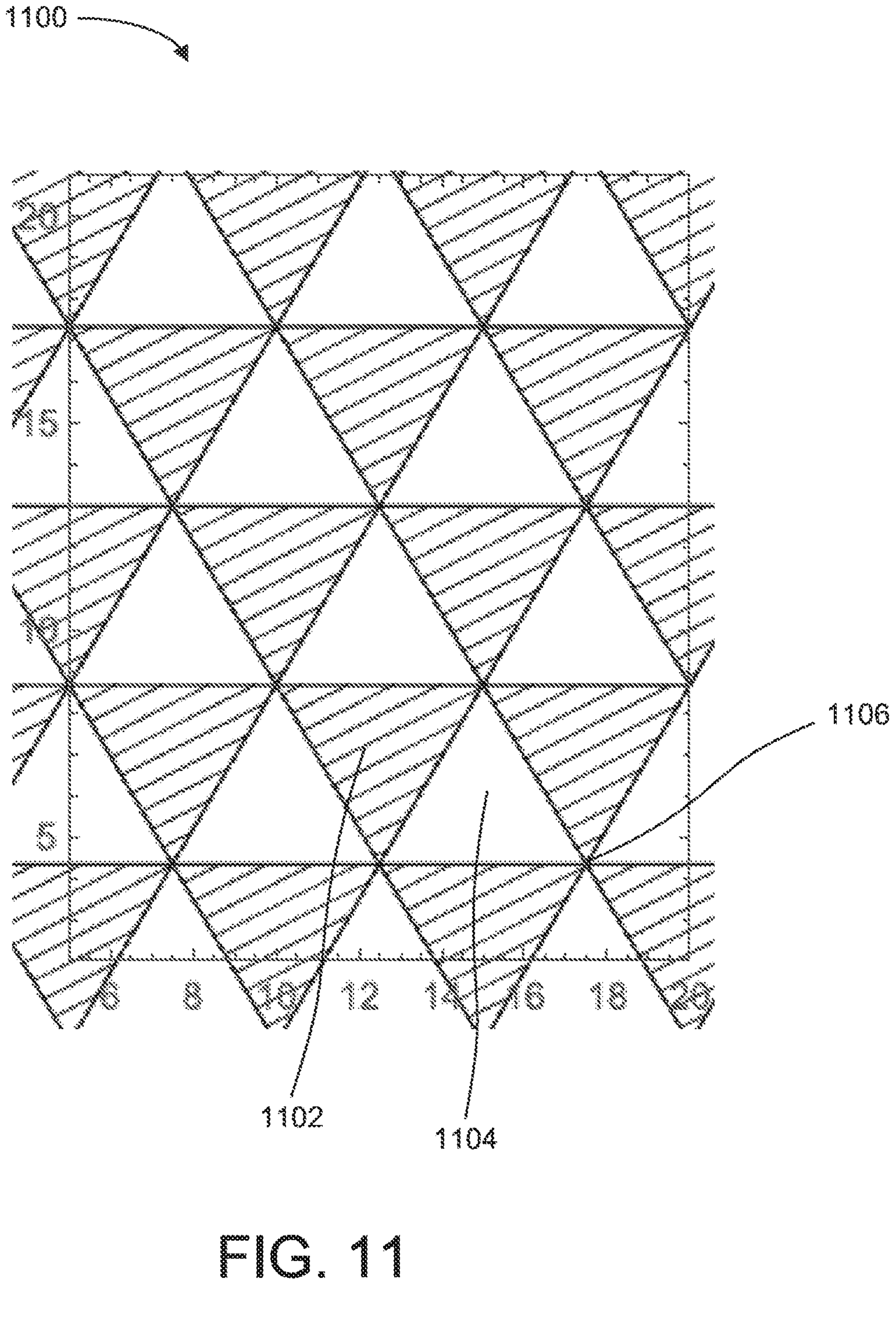
FIG. 11 depicts a point connected treatment pattern with triangular tegulae, according to one or more embodiments of the present disclosure.

In point-connected series, extegs and integs are mathematically point-connected at common vertices (see e.g., 1006 in FIGS. 10 and 1106 in FIG. 11). Extegs (e.g., primary tegulae 1002, 1102 for the first treatment session) are not adjacent to other extegs (that is, they have no common borders), and integs (e.g., secondary tegulae 1004, 1104 for the first treatment session) are not adjacent to other integs. FIGS. 10 and 11 illustrate two point-connected tiling series, which are shaped like regular checkerboards with square 1000 (e.g., FIG. 10) and triangular tegulae 1100 (e.g., FIG. 11). In practice, point-connected series degenerate to skin-island series by erosion at the point-connected vertices. If vertex erosion does not occur during excision, it will occur during healing.

Alternatively, point-connected series can be modified with extra vertex tegulae to prevent vertex erosion. The resulting patterns form useful skin-bridge series.

Skin island series are advantageous because they can completely remove a full-area tattoo in just two TEPR treatments. Point-connected series are another class of two treatment series are based on checkerboard patterns: either square tegulae (FIG. 10), or triangular tegulae (FIG. 11). Both are shown with the same lattice spacing (s=5 mm).

Although theoretically point-connected tegulae produce a new class of tilings (distinct from both the skin-bridge and skin-island series), pragmatically they always degenerate to skin-island series. This occurs either during excision or Subsequent healing when the theoretical point connections at tegulae vertices 1006, 1106 erode and broaden into lanes. TEPR treatment always necrotizes bordering epidermis out to some fraction of a millimeter. Thus, point connections, if they could be constructed, would only be temporarily constructed of dying skin. Point-connected checkerboard extegs become large nodes connecting a tegular net.

Vertex erosion can be inhibited with a three-treatment series. The primary treatment places circular tegula at each theoretical point connection. Secondary and tertiary treatments then take out the hatched and unhatched tegulae. The result is a skin-bridge series. In fact, the embodiment depicted in FIG. 6 does just this. Point-connected series, which stand uneasily between skin-bridge and skin-island series, will either fall into the latter, or can be pushed into the former.

For TEPR tattoo removal, the advanced TEPR process provides Substantial advantages over overlapping series (e.g., FIG. 2). Advanced TEPR processes are full covering. Because they tile a Surface, tiling series can completely cover a full-area tattoo without leaving the uncover defects inherent in overlapping patterns. Advanced TEPR processes minimize retreatment overlap and thereby, inflammation is minimized and the potential for visible scarring is reduced. Advanced TEPR processes are unaffected by skin movement and stretch. Primary healed tegulae are utilized as permanent markers for aligning and defining intermediate treatments (secondary tegulae in skin bridge series). Advanced TEPR processes use templates for accurate layout. Primary and intermediate treatment patterns use templates to ensure accurate layout and alignment. Advanced TEPR processes isolate final ink. The final treatment in a series is technically easy, because all remaining ink has purposely been sequestered within well-sized and isolated extegs. No final template is required. Simply treat the ink. Advanced TEPR processes require a minimum number of treatment sessions. Referring to FIGS. 4-6, embodiments of skin-bridge series require only three treatment sessions. Striped skin-bridge series and skin-island series (e.g., FIGS. 8 and 9) require only two sessions. Advanced TEPR processes reduce the potential for scarring. This occurs because treatment overlap is minimized. Potential for exteg-net Scarring in skin-island series can be reduced with enlarged nodes and offset lanes. Advanced TEPR processes have optimizable areas. Because the first treatment always heals best, a removal series can be optimized by decreasing the area treated with each Successive session. Advanced TEPR processes, which typically employ different removal patterns for each session, are amenable to area optimizing strategies. Advanced TEPR processes are flexible. Advanced TEPR processes are defined by tegulae that tile an area and align to lattices. Lattices can be morphed and resized to accommodate partial-area tattoos and selective removals. Tegulae are simply reshaped to fully cover the tattooed area to be removed.

The discussion so far has been limited to TEPR series for removing full-area tattoos, which technically is the most challenging. Nevertheless, in the tattoo industry complete tattoo removal is far less important than tattoo modification. Of particular importance is the selective removal of undesired tattoo elements in preparation for a cover-up tattoo.

In this regard, the piecemeal nature of tattoo removal using TEPR is greatly advantageous. It uniquely provides the tattoo artist with a new and valuable tool for selective erasure. And although tiling patterns are exceedingly valuable in the full-area removal, they are uniquely suited for selective removal.

Embodiments described herein allow for the construction and use of customized templates. The process for selective removal with regular templates is no more involved than full-area removal. Although any advanced TEPR process can be used, the embodiment of FIG. 6 is assumed. For the first treatment, the primary template 400 is placed over the tattoo element selected for removal. Only primary tegulae 602 that fall within the selected area are marked. Circular tegulae that fall outside and on element borders are not marked. The removal process is then con ducted for the first treatment area. For the second treatment, the secondary template is aligned with the primary, healed skin, polka dots. Extegs that fall within the selected area are marked and TEPR-treated as previously described. Boundary extegs are carefully excised to remove only the tattoo elements selected for removal. For the final treatment, ink remaining within the selected tattoo element is directly removed. Simply treat the ink.

Advanced TEPR processes associate a set of tiling tegulae with every point in a two-dimensional lattice. So far, the lattices described were all regular, being periodic repetitions of a rhomboidal or square unit cell. For full-area removal, regular lattices are adequate and useful. For selective removal, non-regular lattices (without periodicity constraints) are sometimes even more useful.

To custom fit a tattooed area selected for removal, lattices can be stretched and continuously morphed and Some portions can be removed altogether. The tiling tegulae similarly morph to cover the selected area without gaps. Although this can be accomplished with any tiling series, the embodiment described in conjunction with FIG. 6 is particularly useful and easy to use.

Either morph a two-dimensional lattice or uniformly distribute a set of points to cover the tattoo element selected for removal. Primary tegulae are circular disks centered on these points. All remaining tegulae are triangulations of these points with primary disks Subtracted. Lattice points are not placed on the boundaries of the selected area. Instead modified secondary and tertiary tegulae define the boundaries. The only other constraint on point location is that every point must have an even number of nearest neighbors. A point with an odd number of nearest neighbors, would yield two adjacent extegs. Such odd-neighbor problems are easily remedied with point additions and subtractions.

Once the points are located, custom templates are made for laying out primary and secondary treatment tegulae (no tertiary template is required, as the remaining ink is isolated). Custom templates can be cut with computer controlled sheet-cutting machines, or they can be printed and applied as temporary Stick-on tattoos.

As custom templates are computer designed (and then cut or printed), the tattoo geometry must first be input. This data is derived from photographs of the tattoo. Required geometric transformations are facilitated by photogrids.

One problem in using photographs and computers to design tiling patterns and associated templates for selective tattoo removal involves transformations between the curved surfaces of body parts and the flat representations of the images and templates. Mapping an image from a generalized curved surface (like a globe) to a flat sheet is a classic problem that has no perfect Solution: the image is inevitably distorted by whatever mapping is employed.

Fortunately, the great majority of tattoos are placed on body Surfaces that are curved in only one direction, like the surface of a cone. Such surfaces (which everywhere have Zero Gaussian curvature) are said to be intrinsically flat, which means they can be unrolled onto a plane Surface without distortion. A sheet of paper, for example, can (without distortion) be rolled up to form a cylinder or cone.

Although tapered body surfaces are never perfectly flat (in the intrinsic sense), the skin and underlying flesh are pliable and stretchable. This makes it possible to locally apply templates and Stick-on tattoos that are perfectly flat (in the intrinsic sense) without folds or distortions in the appliance, which is relatively unstretchable as compared to skin and flesh. When the appliance is pressed onto the skin, the skin and flesh stretches so that the surface becomes intrinsically flat, just like the appliance. In areas where this is not possible—within concavities or over bony protuberances—the appliance of necessity will wrinkle or fold.

Templates, in some embodiments, include an adhesive side to allow the template to be held in place on the skin of a patient. In some embodiment, separate adhesives or tapes may be used to hold the template in place for marking. In some embodiments, tension bands or straps are used to hold the template in place. Some embodiments may use spring loaded clips, mechanical hoods and loops, magnets, or any other mechanism for quickly, securely, and easily attaching the templates to the patient.

Because an applied template intrinsically flattens the underlying flesh, which otherwise is not intrinsically flat, knowing the unstretched Surface geometry of the tattooed body part is not useful. So even though the geometry of the tattooed body part can be precisely measured (by laser scanning, for example), the results are not useful. Instead, the geometry of the tattooed body part must be measured after it is intrinsically flattened by an unstretchable appliance.

This measurement is facilitated by photogrids, which are transparent, relatively unstretchable, appliances overprinted with a grid of thin lines. The color of the grid lines is chosen to stand out against the tattoo it covers. The precise shape and size of the grid is immaterial as long as it is well-known (a one-centimeter square grid is adequate), and the grid itself can be replaced by an array of discrete dots or crosses, or any other well-defined alignment pattern.

A photogrid is placed on the skin over the tattoo. Photographs are taken, often from several angles if the tattoo wraps around a curved body surface. The grid locates points on the tattoo, which are used to mathematically unwrap the intrinsically flattened tattoo from the body surface.

This unwrapping transformation is not difficult. Photogrid locations are first located by image processing. The image is then morphed until all the grid locations (located in the image) return to their original positions in an extrinsically flat plane.

The extrinsically flattened tattoo image (that is, it now lies on a plane) is then used in the custom template design process. Once this is complete, the template is directly cut or printed without any other geometric trans formations. When the resulting template is applied over the tattoo, it will intrinsically flatten the skin precisely as did the original photogrid.

A custom templating process may include various steps including:

1. Photograph the tattoo overlaid by a photogrid applied to the skin;
2. Import the photograph into a computer via a computer program;
3. Image process the photograph to find the photogrid alignment markers;
4. Morph the image so that the photogrid alignment markers overlay their original grid positions on an extrinsically flat Surface. This morphing flattens the tattoo image (producing a morphed image);
5. Display the flattened tattoo image, so the technician can outline the tattoo elements selected for removal;
6. Once the removal region is defined, the computer program generates a custom tiling series (and potentially custom primary and secondary templates);
7. Primary and secondary templates are directly cut or printed by computer-controlled, commercially-available devices;
8. For the first treatment, the primary template is aligned with the selected tattoo element and then TEPR treated;
9. For the second treatment, the secondary template is aligned with the primary, healed-skin, polka dots. Extegs that fall within the selected area are marked and TEPR treated as previously described. Boundary extegs are carefully excised to remove only the tattoo elements selected for removal;
10. For the final treatment, ink remaining within the selected tattoo element is directly removed. Simply treat the ink.

FIGS. 1-2, and 4-11 depict scales on the x-axis and y-axis in millimeters. Although drawn to scale, embodiments may include varying size of apertures and varying distances between apertures are not limited to the scale of the drawings depicted and described herein.

Keratinocytes proliferate to cover a fresh wound at rates determined by the natural growth and cell-cycle time governing mitosis (non-gametic cellular division). Thus, when the minimum linear or areal extent of the wound is large, epithelialization is delayed. This can result in fibrosis, hypertrophic scarring, and poor healing. A goal of tissue disruption, including microneedling, may be to produce wounds in spatial patterns that are conducive to both healing and minor blood scabbing. When wounds are too small, the disruption process may not be effective. When wounds are too large, the skin may be damaged, and scarring may prevail.

Figure 12:
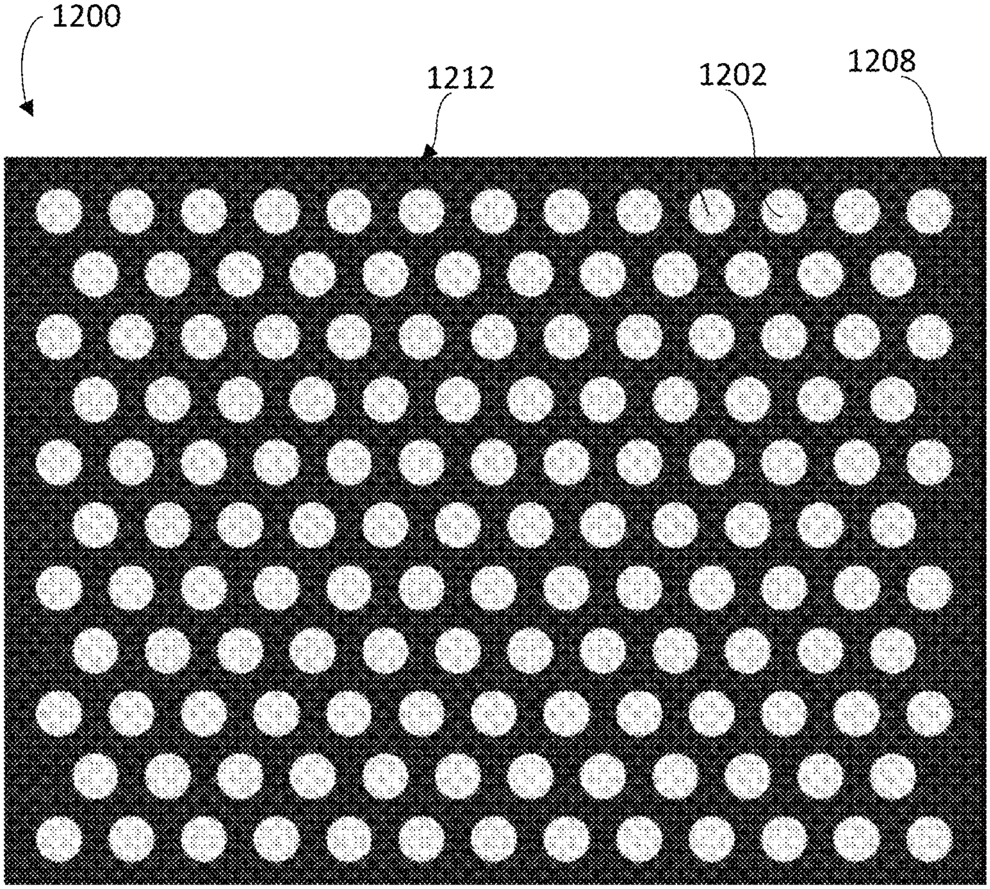
FIG. 12 depicts a template with a rhomboid pattern of circular apertures, according to one or more embodiments of the present disclosure.
Figure 13:
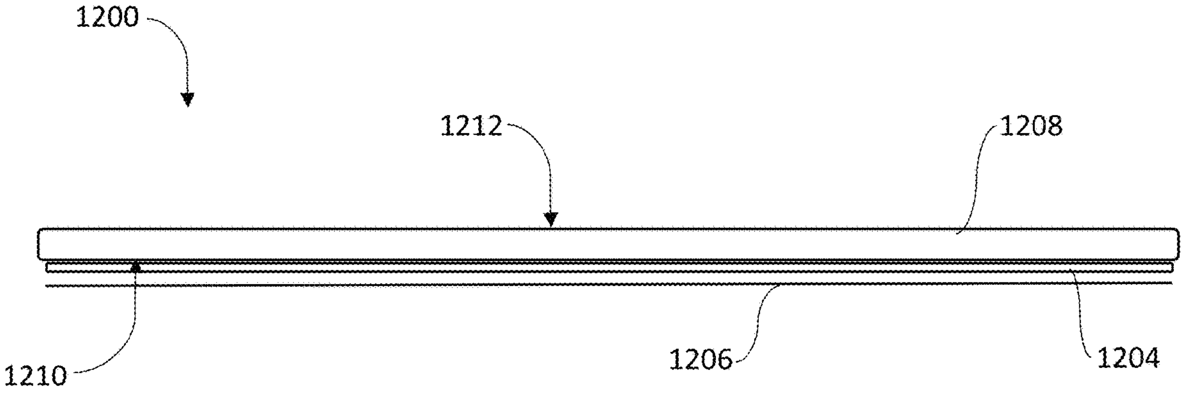
FIG. 13 depicts a side view of the template of FIG. 12 with a release liner detached.

Referring to FIGS. 12-13, in one embodiment, a template 1200, which may be adhered to the skin, is used to control the depth of a needle group, prevent lateral wandering of a needle group, and create a structured, patterned procedure to remove skin irregularities. For example, skin irregularities that may be removed include skin lesions, pigmented lesions, scarring, acne, stretch marks, or any other irregularity of the skin. Skin irregularities can be removed through a micro or macro needling process. Puncturing the skin with, for example, a microneedle can encourage the skin to produce new skin in its place.

Puncturing the skin may involve a group of small needles, or individual needles, that puncture the epidermis and dermis at a predetermined depth. When the epidermis and dermis are punctured, the underlying cells, epidermal cells and dermal fibroblasts, are only minimally damaged, which creates a minor immune response initiating blood flow to the dermis. After the epidermis and dermis have been punctured, immune cells (white blood cells) and transforming growth factor beta-3 are stimulated and are necessary in the creation and regulation of new cell growth. Further, the puncture channels created by the microneedles, or other puncturing devices, stimulate fibroblasts to create new collagen, allowing the epidermis to have a smoother, fuller surface and better elastic properties after the healing process. The depth and pattern of the needle group is important. The correct depth of the needle group and pattern of puncturing can lead to effective collagen production and healing. Without the template 1200, a user is left to determine their own pattern to puncture the epidermis and dermis, which may lead to areas of the skin that have been punctured too much or not enough. A user may also puncture the skin too deep causing significant trauma to the underlying cells and reducing the effectiveness of the treatment.

Accordingly, it may be advantageous to use a template that has a thickness that can assist a user in controlling the depth of a needle, allowing a user to puncture the epidermis and dermis at a consistent depth. It should be noted that the depth of the needle group may also be adjusted on the needle device. The template 1200 comprises a plurality of needle apertures 1202 to create a structured procedure, an adhesive layer 1204, and a release liner 1206. The release liner 1206 may be removed, exposing the adhesive layer 1204, so that the template 1200, with the plurality of needle apertures 1202, may be positioned over the skin irregularity. The template 1200 can provide a structured approach to removing many skin irregularities and tattoos found on the epidermis.

Figure 14:
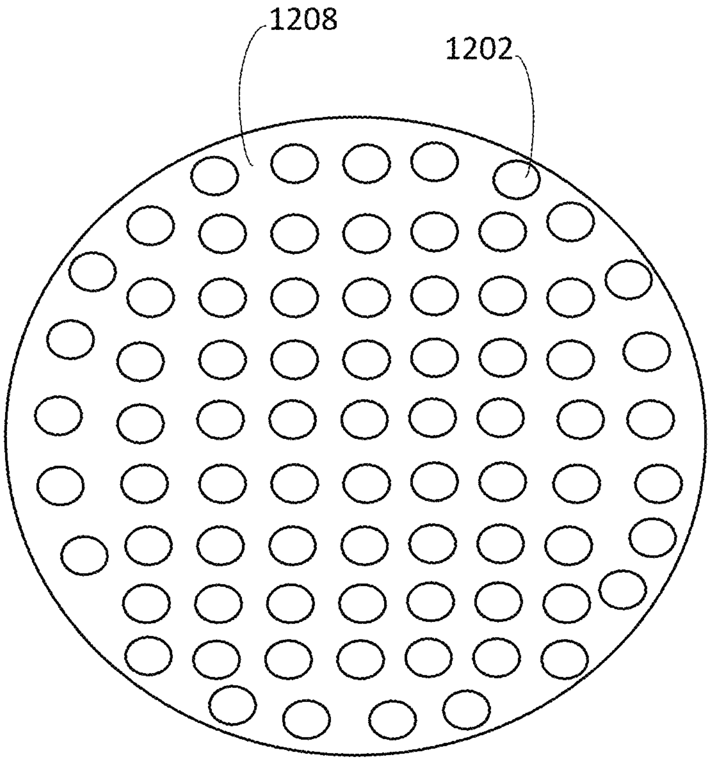
FIG. 14 depicts a top plan view of a circular template, according to one or more embodiments.
Figure 15:
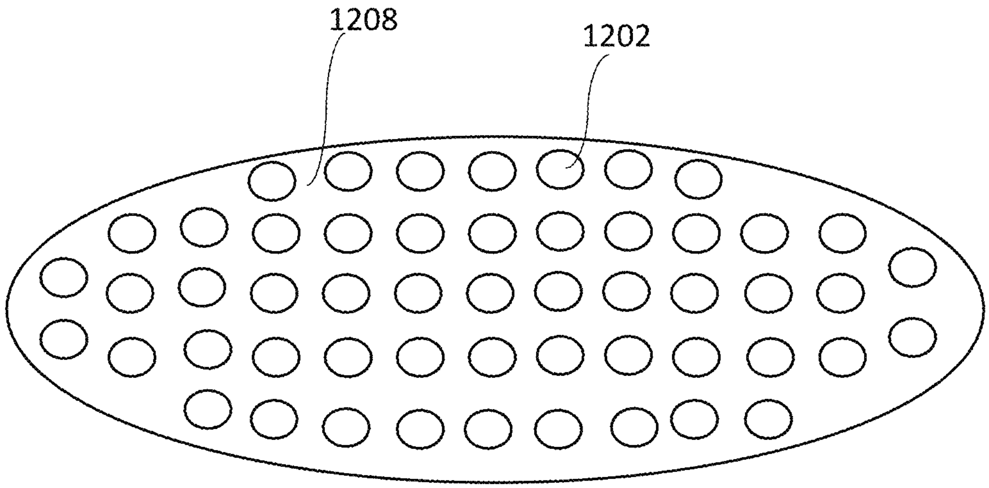
FIG. 15 depicts a top plan view of an oval template, according to one or more embodiments.

The template 1200 can be square shaped; however, it will be appreciated that the template 1200 can be many other shapes, such as circular (FIG. 14), rectangular, etc. Further, it will be appreciated that, in one embodiment, the shape of the template 1200 may be similar in shape and size to the skin irregularity to provide the most control during a procedure. For example, as shown in FIG. 15, an oval shaped template may be used with a long skin irregularity on the epidermis so that the entire skin irregularity is covered, without having too much template overlap onto non-irregular skin.

The template 1200 may be a sheet of material 1208, which may be made of silicone, polypropylene, or any other material. In some embodiments, the sheet of material 1208 may be flexible to conform to a non-flat surface of skin on a patient. In some embodiments, the sheet of material 1208 may be flexible while not stretching. That is, the distance between the plurality of needle apertures 1202 does not increase through stretching in a transverse direction between the plurality of needle apertures 1202. In some embodiments, the template 1200 is cut or missing portions of the sheet of material 1208 in order for the template 1200 to conform to any shape of skin irregularity or protrusion of the epidermis, such as the nose or chin.

The template 1200 may vary in length, width, and height. There may be, for example, a template that is 1"×1", a template that is 6"×6", or any other sized template. In one embodiment, the template 1200 may be ⅔ inch×1 inch, with the needle apertures being 1.67 mm diameter disks, which are spaced apart 2.67 mm from the center of the aperture. In addition, the needle apertures may combine to cover approximately 35 percent of a unit cell, and the total count of needle apertures is 138.

The thickness of the template may assist a user in controlling the depth of the needle or needle group. In particular, the needle apertures 1202 control the depth as discussed below. Accordingly, controlling the depth of the needles assists a user in different procedures and provides the optimal puncture depth, a depth where cell damage is limited. This can allow for improved effectiveness in the disruption process, and a quicker healing of the dermal and epidermal layers. It should be noted that the depth of the needle or needle group may also be controlled by extending and retracting the needle group on a needle device, which can add more control and adjustability in puncturing the epidermis and dermis.

In one embodiment, the thickness of the template may vary from one side to the opposite side to account for variations in the depth of the epidermis, especially on the face. If a skin lesion covers the thin and thick epidermal areas of the face, a user may not be able to use the same depth for the needle group due to the variations in epidermal thickness. For example, one side of the template may be thin in order to offer a greater puncturing depth on the thicker flesh above portions of the mandible, while the opposite side may be thicker in order to offer less puncturing depth for thinner flesh positioned over the sphenoid or frontal bones.

Figure 16:
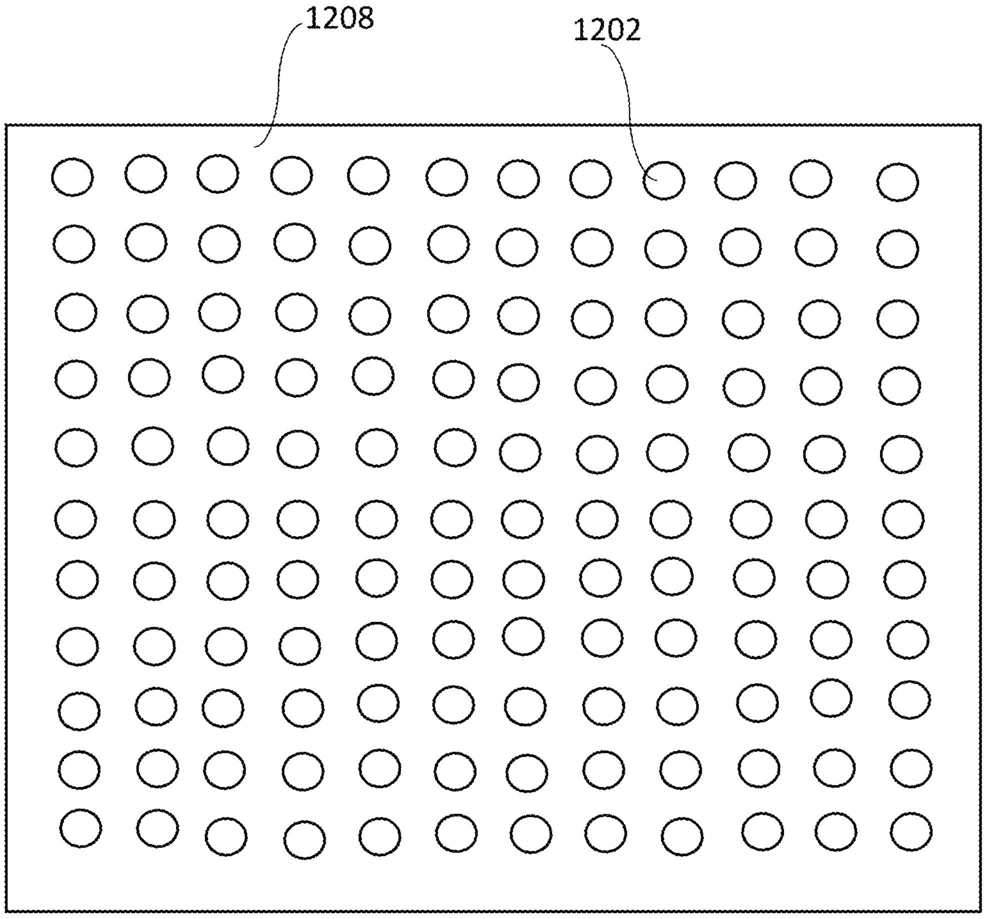
FIG. 16 depicts a top plan view of a template with circular apertures, according to one or more embodiments.

Further, the template 1200 may include the plurality of needle apertures 1202. The plurality of needle apertures 1202 may be disk shaped and spaced in a rhomboid pattern. The plurality of needle apertures 1202 may be small; however, they may also be large or any other size. In addition, as shown in FIG. 16, the plurality of needle apertures 1202 may be evenly distributed on the template 1200 in a linear pattern. In some embodiments, the plurality needle apertures 1202 may be in other patterns and shapes, such as a circular pattern with square apertures or circular apertures. It should be noted that the patterns and shapes of the needle apertures may be in any pattern or shape to assist a user.

Referring back to FIG. 12, the plurality of needle apertures 1202 can provide a location for a needle group to enter the epidermis and dermis, for example, to remove a skin irregularity through simply puncturing the epidermis and dermis to stimulate collagen production, or to introduce fluid, via the puncture channels, to remove a tattoo, such as a shallow tattoo in the eyebrows. The plurality of needle apertures 1202 are of a diameter that is large enough to allow the needle or group of needles to enter, but small enough to prevent a needle cartridge tube from entering. This allows a controlled procedure where a user can insert the needle group to the same depth, until the needle cartridge tube contacts an upper surface 1212 of the template 1200, in each of the plurality of needle apertures 1202. Further, in an alternate embodiment the plurality of needle apertures 1202 may be useful in preventing damage to the epidermis. For example, each of the plurality of needle apertures 1202 may receive the cartridge tube, securing the cartridge tube and the needle group in a single location and preventing lateral movement. This would prevent the needle group from wandering laterally across the epidermis. Additionally, a user must lift the needle group above the upper surface 1212 of the template 1200 in order to place it in another needle aperture, which prevents the user from accidentally dragging the needle group across the epidermis. In contrast, without the template 1200, a user may drag the needle group, or the needle group may wander when performing the puncturing procedure, causing damage to the epidermis. It will be appreciated that the needle apertures 1202 can be a variety of shapes, patterns, and sizes so as to receive numerous gauges of needles and be used on a variety of skin irregularities or tattoos.

The adhesive layer 1204 (FIG. 13), on a lower surface 1210 of the sheet of material 1208, allows the template 1200 to be held in place on the skin of a patient. The adhesive layer 1204 may comprise any suitable adhesive. For example, the adhesive layer 1204 may be an acrylate, including methacrylates and epoxy diacrylates. Alternatively, the adhesive layer 1204 may be a silicone based adhesive. The adhesive layer may be coextensive with the lower surface 1210, in a pattern, or any other manner on the lower surface 1210 surrounding the plurality of needle apertures 1202. In some embodiments, separate adhesives or tapes may be used to hold the template in place. In some embodiments, tension bands or straps are used to hold the template in place, or any other mechanism for quickly, securely, and easily attaching the template to the patient. Further, the release liner 1206 may releasably adhere to the adhesive layer 1204. The release liner 1206 may protect the adhesive layer 1204 from prematurely adhering to an undesired location and may be removed from the template 1200 prior to application on the epidermis.

To use the template 1200, a user would remove the release liner 1206, exposing the adhesive layer 1204. Then the user would apply the template 1200 over a skin irregularity on a patient. The user can then systematically place the needle group into each of the plurality of needle apertures 1202 to puncture the skin to a depth until the needle cartridge tube contacts the upper surface 1212 of the template 1202. Once all of the plurality of needle apertures 1202, or a portion of the plurality of needle apertures, have been addressed, the user can remove the template 1200. This process could be performed multiple times. For example, after the first treatment, the user can move the template 1200 and repeat the same process, which can lead to more collagen production and ridding the epidermis of skin irregularities. Specifically, in a second treatment the user could move the template 1200 so that the plurality of needle apertures 1202 overlap the previously punctured skin channels. It should be noted that a second treatment may not need to be a full treatment. For example, the second treatment may only require that half, or any other amount, of the plurality of needle apertures 1202 be addressed by the needle group. After the treatments, new collagen and epidermis can begin to replace the skin irregularity.

Figure 17:
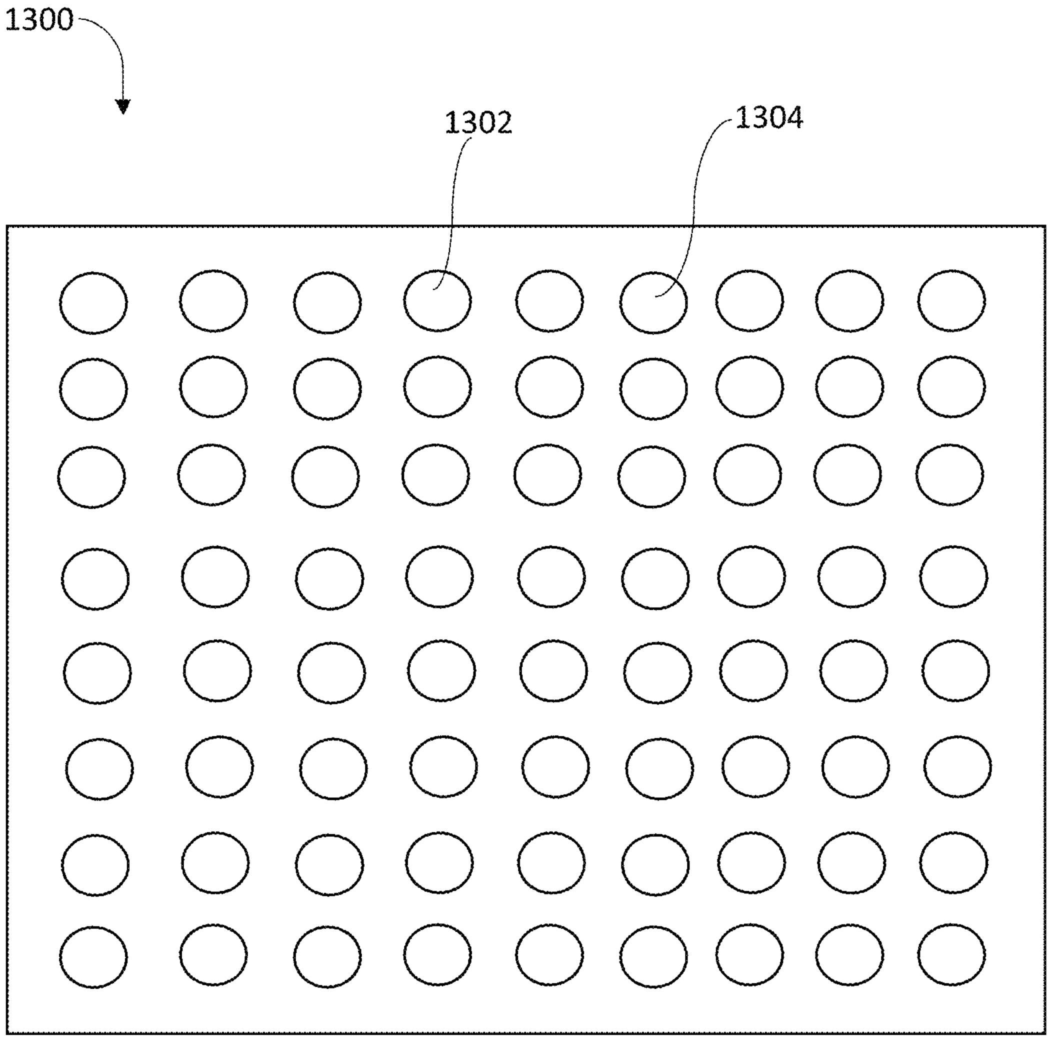
FIG. 17 depicts a top plan view of a template with a plurality of large needle apertures, according to one or more embodiments.

Referring to FIG. 17, in one embodiment, a large template 1300 comprises a plurality of needle apertures 1302, wherein the plurality of needle apertures 1302 are large apertures 1304. The large apertures 1304 may accommodate macro needles, large microneedle groups, or other larger needles. In some circumstances, macro needles can be used to increase collagen production for large areas of skin. At times, the larger needle apertures and larger template could be used to stimulate collagen and elastin production to remove, for example, wrinkles. It should be noted that the increase in needle size can also mean an increase in tubing size. While the tubing size increases, it will be prevented, like the smaller tubing, from entering the needle apertures in order to control the depth of the needle group.

Trans-epidermal pigment release (TEPR) is a non-laser process for removing tattoo ink. TEPR can be implemented with many varied tissue-disruptive technologies. TEPR employs partial thickness dermal injuries to initiate a beneficial healing response. These are superficial injuries that penetrate into but not through the dermis. The beneficial response is the formation of an eschar or debris-scab of necrotized dermal tissue. Tattoo ink is pushed out of the skin from below by the healing and regenerating epidermis and dermis.

TEPR is most effective when injuries are localized to areas of skin bordered by uninjured skin. Embodiments described herein utilize templates to outline treatment areas of the skin and limit them to a specific size and shape that balances the need for bordering uninjured skin and a sufficient area to apply the TEPR process.

Keratinocytes are the cells responsible for the structure and barrier functionality of the cellular epidermis. A fresh wound (lacking a protective epidermis) is quickly covered by proliferating keratinocytes spreading (beneath the temporary scab) from non-necrotized, bordering tissue. The bordering uninjured skin is important to the healing process. A wound becomes fully epithelialized when the thin layer of keratinocytes completely recovers the wound. This typically occurs within 2 to 3 weeks of the injury. After epithelialization is complete, the stratified layers of keratinocytes (found in mature epidermis) regenerate, while other cells in the dermis rebuild the underlying dermal matrix structure. Epidermal maturation requires months for completion, such as two to three months. The underlying dermal matrix is rapidly rebuilt with oriented fibers (characteristic of tough scar tissue), which are later remodeled over years into more pliable tissue. During dermal rebuilding, visible and hypertropic (raised) scars can form depending on the depth of the wound, genetic susceptibilities, and aftercare (such as attempting to control trans-epidermal water loss and dermal stresses).

Keratinocytes proliferate to cover a fresh wound at rates determined by the natural growth and cell-cycle time governing mitosis (non-gametic cellular division). Thus, when the minimum linear or areal extent of the wound is large, epithelialization is delayed. This can result in fibrosis, hypertrophic scarring, and poor healing. The goal of TEPR is to produce wounds in spatial patterns that are conducive to both healing and eschar formation. When wounds are too Small, ink-agglomerating eschars will be limited or will not form. When wounds are too large, the skin will be damaged and scarring will prevail. Embodiments described herein utilize templates to mark potential treatment areas to optimize the size and shape of wounds.

Because TEPR treatment always occurs locally at sites bordered by untouched skin, tattoos should be removed piecemeal in isolated tegular patterns. A series of treatment sessions, each separated by inter-session healing periods (lasting approximately from 8 to 12 weeks), are utilized to completely remove a tattoo.

It will be appreciated that a variety of tissue-disruptive technologies may be used for removing tattoos or any skin irregularity. Accordingly, the following paragraphs discuss various tissue-disruptive technologies that may be employed in patterned escharotics.

In some embodiments of patterned escharotics, mechanical approaches may be utilized to disrupt the tissues. For example, needling, abrading, cutting, or any other mechanical approach may be used to disrupt the tissue and promote tattoo removal and/or skin rejuvenation. Specifically, tissue disruption affects the inked dermis to a certain depth and the overlying epidermis. Mechanical tissue disruption may be accomplished by dermabrasion, including burrs, brushes, or the use of other abrasive material. Dermabrasion uses transverse motions to destroy tissue, which may ultimately remove the tissue. In some instances, needling may be used for dermabrasion depending on how the substrate is moved through the tissue. The response to mechanical skin disruption is the formation of an eschar of necrotized dermal tissue, thereby promoting tattoo ink removal or skin irregularity removal. In particular, through TEPR the inked dermis is disrupted, but the inked dermis is not removed. Accordingly, the inked dermis is removed by the formation and expulsion of the eschar, which has agglomerated the inked and disrupted tissue.

In some embodiments, hot or cold probes may be used to disrupt the tissue by changing temperature. Thus, tissue disruption via temperature destroys inked tissue, promoting the formation of an eschar to remove the ink. The temperature of the probe and the probe dimensions may be used to control the depth of tissue disruption.

Additionally, various chemical agent may be used to disrupt the tissue to induce an eschar. As an example, acids may be used to necrotize cells and disrupt the extracellular matrix, thereby inducing the body's healing process. The depth at which the chemical may enter the dermis depends on the molecular properties of the of the chemical, the quantity or strength of solution, and the means of distributing the chemical (i.e., injector mechanics). Biological approaches may also disrupt the tissue. This can be achieved by controlling signaling molecules, such as peptides, or using organisms, such as bacteria, to break down cell walls. As discussed with chemical techniques, biological approaches may control the depth by the quantity of biological material, injector mechanics, as well as the signal/organism properties. Accordingly, depending on the type of signal or organism, will determine the amount of biological material and the means of introducing it into the tissue.

Other tissue-disruptive technologies may include equilibrium ion and cold plasma ion. Equilibrium ion may disrupt the tissue via an electric driven field (AC or DC) where depth is controlled by frequency and probe dimensions. Similarly, cold plasma ion may disrupt the tissue by using an electric driven field. Frequency, duty cycle, and probe dimensions control the depth and thus, may be adjusted according to the tattoo or the skin irregularity.

Further, focused waves and focused particles can disrupt tissue to produce eschars. In particular, focused waves use wave-like radiations, such as ultrasound, lights (e.g., incoherent light), lasers, to disrupt tissue. To control the depth at which the focused waves enter the tissue, a user may adjust the wave frequency and the aperture where the focused waves are emitted. Many frequency ranges may be used, such as microwave, infrared, visible, or ultraviolet. On the other hand, focused particles use particle-like radiations, such as X-ray, gamma ray, alpha, proton, electron, neutron, etc. to disrupt the tissue. Depth of the focused particles in the tissue may be determined by the radiation type and the emitter geometry.

Another tissue-disruptive technology utilizes directed radiation. Directed radiation comprises visual and non-visual wavelength energy, which energy may be coherent or non-coherent. It will be appreciated that particular wavelengths of the visual and non-visual wavelength energy have previously been used for tattoo removal. Directed radiation may be delivered to the surface of the skin to be treated by waveguides or direct impingement. When the directed radiation contacts the skin, the radiation disrupts and necrotizes the inked dermal tissue, which induces the healing response that agglomerates the inked and dead tissue in eschars. Thus, the eschars are pushed up and out by reforming the epidermis and dermis under the eschar. The eschar may be formed at the treatment site, such as the tegula site.

In some embodiments, tissue molecular bond disruption may occur via direct impingement. For example, direct impingement may disrupt tissue by using high energy delivered at high repetition cycles to cause the tissue disruption. A specific example may include ocular corneal tissues and femtosecond laser pulses with high energy. Other approaches of disrupting the tissue may involve burning the tissue to create eschar formation as found in third degree burns with non-directed energy or with accidental burns. It will be appreciated that numerous energy delivery ranges may be acceptable for TEPR.

To deliver the directed radiation to the tissue, a pattern may be used. Patterns for energy delivery may be created by scanning methods involving mechanical pattern generators, such as galvanometer mounted mirror arrays to pattern the directed energy or dispersion of light in pattern formations. When light is used, the pattern may be controlled, allowing the scale or size of the treatment area to ensure healthy tissue bridges remain. In some embodiments, cooling the tissue surface prior to surface treatment when using directed energy treatment can help to ensure that tissue bridges that need to be maintained between tegula are protected during the treatment cycle and that any heating, burning, or removal is limited to treatment sites.

Other patterns for delivering directed energy to the tissue may comprise optical capture methods based upon a scan of the area to be treated and subjecting this image to an image processing software program that determines the shapes, sizes, times, depths, and frequency of the treatment. In one embodiment, the patterns created by this type of programming could be scaled and manipulated by algorithms within the code to place more treatment on deeper pigmented areas, and less treatment on lighter pigmented areas. Accordingly, less pigmented areas would receive less energy than deeply pigmented areas. It will be appreciated that this approach may help relieve some of the pain associated with treatment parameters rather than treating the overall treatment site at one setting or one energy level. The algorithm may also take into consideration that some pigmented areas and colors of a tattoo absorb light more efficiently than other pigmented areas. Furthermore, the algorithm may consider a patient's skin pigment, which would promote maximum tissue reaction for minimal energy delivered. It should be noted that any type of template, such as a physical template or scan, may be used with TEPR.

Another advantage to the patterns described above is smaller diameter treatment areas. For example, in one embodiment, the smaller, more focused treatment areas may provide high energy treatment so as to remove deep blue or black inks. Thus, smaller treatment areas and deeper treatment may be employed in selected areas of the overall tattoo. It should be noted that the tegula employed over the treatment site may vary in diameter and depth from one location of the tattoo to another based upon scans and best calculated treatment options. Accordingly, deeper pigment areas may possibly be treated in the same amount of time as less pigmented areas by varying the energy level used. Overall, pain may be more manageable because the pain is localized into small areas of the treatment site. Furthermore, it will be appreciated that TEPR is capable of removing ink independent of color or composition.

In one embodiment, unique patterns developed by an algorithm for custom treatment for tattoo removal can be located and registered on a patient and reproduced for each treatment cycle on the treatment area by the patient's natural features. In particular, a patient's moles, freckles, or other unique feature may assist in the production of the treatment area. Using these naturally occurring locations as registration marks, allows the patterns used for the initial treatment to be altered, and evaluated each time to ensure the tissue bridges are maintained, areas of treatment are monitored to ensure that ink removal is occurring as planned, and recovery is occurring as designed during the treatment.

Furthermore, with direct impingement, the epidermis of the patient may be treated, in some embodiments, with a photoreactive fluid or chemical either sprayed or wiped on the surface prior to treatment, enhancing reception and disruption of tissue using the directed energy. Patients that may have skin that does not absorb energy as readily (i.e., light pigmented patients) may need the photoreactive fluid. It should be noted that the photoreactive fluid may assist in raising the energy level of the surface of the epidermis so as to cause more rapid disruption or burning, lowering treatment and exposure time, and lowering the pain level that accompanies longer treatment times and heat loads.

Additionally, in some instances a reflective template may be used on areas that are not treated, with the intent of resisting energy deposition in those areas. For example, the reflective template may remain in place during treatment and may comprise an energy reflective coating on a top surface. Accordingly, the energy, focused at a certain depth, may be scanned over the reflective template and over the apertures to induce tissue disruption only within the apertures. Further, in some embodiments, an image may be projected onto the skin, where a user may place fluid or medium that when exposed to certain light wavelengths, cures or colors the medium, creating a template on the skin.

While various examples of tissue-disruptive technology have been discussed above, it will be appreciated that any other form of tissue disruption may be used in patterned escharotics. Furthermore, it should be noted that the different tissue-disruptive technologies can be employed with different treatment patterns. Templates, as discussed herein with respect to various embodiments, provide indicia upon the skin of a patient to define a treatment area composed of tegulae. Such templates may comprise any appropriate method that provides indicia on the skin in order to define the tegulae. Examples of potential templates include physical templates as discussed herein, including preformed and custom templates, as well as transparent templates, opaque templates, reflective templates, etc. Alternatively, other templates maybe used, including projected images that may be created by analog and digital scanning. In addition, templates may be generated digitally or virtually, and applied by creating a physical template, projecting a template, presenting a template to a practitioner in augmented reality, or programming appropriate trajectories into computer controlled device, or any other method of providing indicia of the size and shape of the tegulae as would be understood by one of ordinary skill in the art.

TEPR may be used in many applications. One example involves the removal or modification of permanent makeup tattoos. In particular, permanent makeup used to define eyebrows may be removed or modified by using TEPR and covering templates. As described below, various covering templates may be used to mark tegulae for TEPR for tattooed eyebrows.

Figure 18:
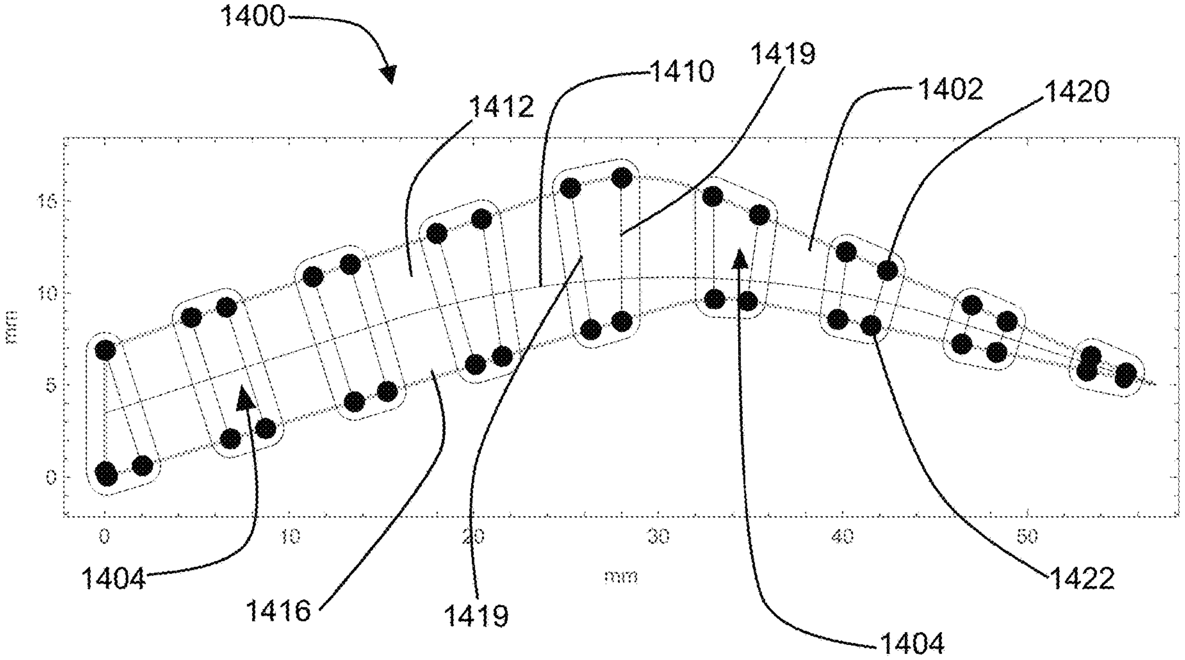
FIG. 18 depicts a top plan view of a primary template with primary apertures.
Figure 19:
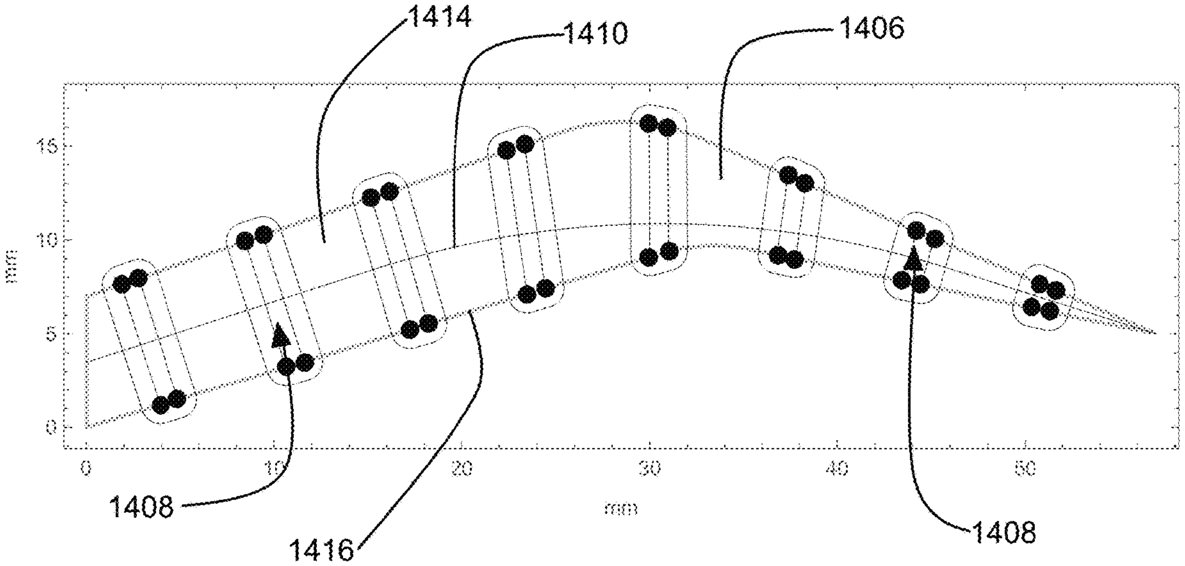
FIG. 19 depicts a top plan view of a secondary template with secondary apertures.

Referring to FIG. 18, in one embodiment, a system for removing tattooed eyebrows 1400 comprises a primary template 1402 with primary apertures 1404. The primary template 1402 may be used to mark or layout the first or primary TEPR treatment and primary tegulae. A secondary template 1406, as shown in FIG. 19, comprises secondary apertures 1408 to mark or layout a second treatment and secondary tegulae. Accordingly, the primary tegulae may be TEPR treated during a primary treatment and the secondary tegulae may be TEPR treated during a secondary treatment. Both the primary and second apertures 1404, 1408 comprise a striped pattern that may create an overlap of alternating primary and secondary apertures. The striped pattern allows a tattooed eyebrow to be removed in two treatments, while others pattern may require three treatments. However, in some embodiments, the primary and secondary apertures 1404, 1408 may comprise circular or other types of patterns. It will be appreciated that, in some embodiments, only the primary template 1402 is used in a TEPR treatment because only two TEPR treatments may be required to remove a full-area eyebrow tattoo with a striped pattern. Accordingly, after the first treatment, the second treatment is shown by the remnant ink as the TEPR removal targets.

In any series of TEPR treatments, the primary treatment always causes the least dermal trauma. As a consequence, the most removal work possible should be performed during the primary treatment. This means that the width of the primary apertures 1404 is greater than the width of the secondary apertures 1408. Furthermore, the primary apertures 1404 may be tapered to bend the striped pattern along a curved camber line 1410 of the primary templates 1402. Alternatively, in some embodiments, the primary apertures 1404 may not be tapered. True perpendiculars fall in the gaps midway between adjacent apertures. Near perpendiculars defining the primary apertures 1404 are located at distances ±(gap/2+radius) from the true perpendiculars. This construction ensures that the gaps between adjacent primary apertures are uniform, without any taper.

Figure 20:
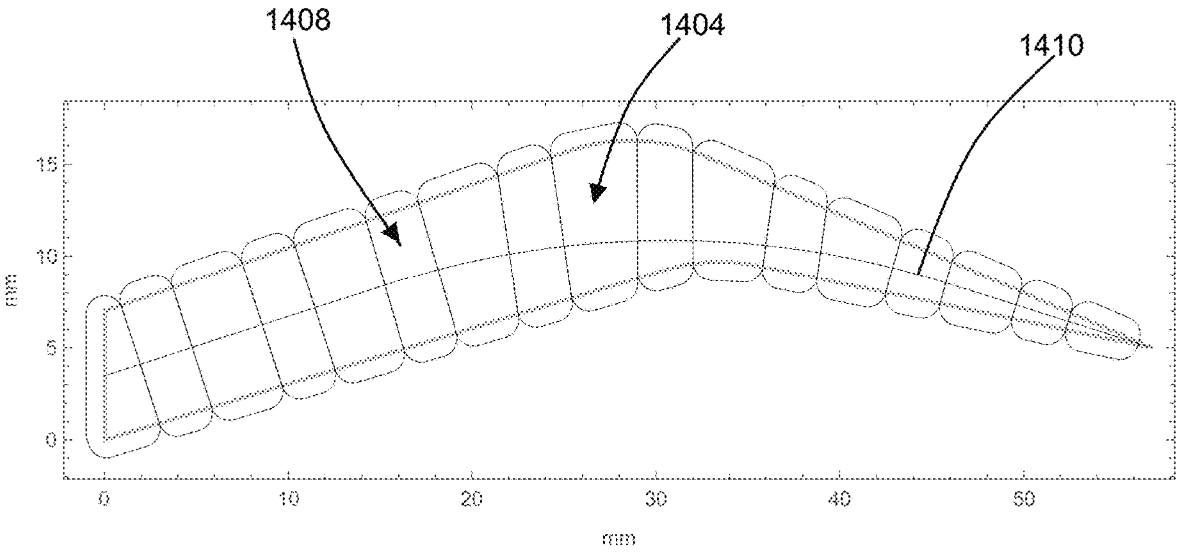
FIG. 20 depicts primary and secondary apertures of a primary and secondary template.

Further, as shown in FIG. 19, the secondary apertures 1408 on the secondary template 1406 fill the space between primary apertures 1404 (see FIG. 20). As a consequence, the secondary apertures 1404 may have the same uniform width (without any taper), while the gaps between adjacent apertures are tapered. It should be noted that because the primary apertures 1404 have a width greater than primary inter-aperture gaps 1412, the opposite is true for secondary templates 1406. In other words, the secondary inter-aperture gaps 1414 have a width greater than the secondary apertures 1408. The secondary apertures 1408 are positioned to cover the primary inter-aperture gaps 1412.

Although secondary inter-aperture gaps 1414 taper, they can be made large enough so that the minimum secondary inter-aperture gaps 1414 always exceed the minimum primary inter-aperture gaps 1412. As will be appreciated, this ensures that skin bridges separating cut TEPR tegulae will not narrow and cause tegula merging, which merges are detrimental to healing. Further, it will be appreciated that the primary and secondary templates 1402, 1406 may change in size, shape, and orientation to address all shapes and sizes of tattooed eyebrows. Additionally, a border 1416 may define an area that the primary template 1402 and secondary template 1406 may cover.

Referring back to FIGS. 18-19, described below is an example of constructing and defining apertures on the covering temples described herein. The primary and secondary apertures 1404, 1408 may be of a variety of shapes and sizes and be rounded quadrilaterals. That is, the primary and secondary apertures 1404, 1408 may be four-sided figures with rounded corners. It will be appreciated that the primary and secondary apertures 1404, 1408 and other covering template apertures may comprise rounded corners to accommodate the TEPR wire brush, which has needles configured in a compact six-around-one cluster that is about one millimeter in diameter. Accordingly, the rounded quadrilaterals are closed curvilinear figures defined by four circular arcs tangent to four interconnecting line segments. Every rounded quadrilateral is completely defined by the centers of the four arcs (upper dots 1420 and lower dots 1422 in FIG. 18) and the four arc radii. All embodiments described hereinbelow may comprise rounded corners with the same radius as described above. Given a common corner radius only the center points locating the rounded corners need be specified to complete the construction of the template apertures.

Rounded-corner center points lie at the intersections of the primary and secondary borders 1416, 1418 with near perpendiculars 1419 to the central camber line 1410 on both the primary and secondary templates 1402, 1406. These near perpendiculars 1419 are represented by the line segments connecting upper and lower dots 1420, 1422. To keep the gap between apertures constant without any taper (so that TEPR cut skin bridges will have uniform widths), adjacent aperture sides and their associated near perpendiculars must all lie parallel to one another. They also lie parallel to a true perpendicular to the camber line 1410, which for primary templates 1402 always lies in the gap midway between adjacent apertures.

The curvilinear camber line 1410 defining the striped pattern bisects both a head of the primary template (the truncated left end in FIG. 18) and a tail of the primary template (the pointed right end in FIG. 18). These two bisecting lines are connected by a tangent curve with a radius chosen to appropriately fit the eyebrow shape.

Once a camber line is constructed, the intersections of true perpendiculars are spaced by arc length along the camber line. Two arc lengths measured along the camber line 1410, the primary aperture width and the primary gap between adjacent apertures, establish these points. Once the true perpendiculars are established, the parallel near-perpendiculars 1419 can be established, which define the primary apertures. FIG. 18 illustrates the primary template pattern covered with striped primary apertures 1404 that exactly covers a particular eyebrow shape. In primary templates 1402, and as previously discussed, the primary gaps 1412 between the primary apertures 1404 (which maintains the skin-bridging distance) are designed to be uniform, without any taper.

Figure 21:
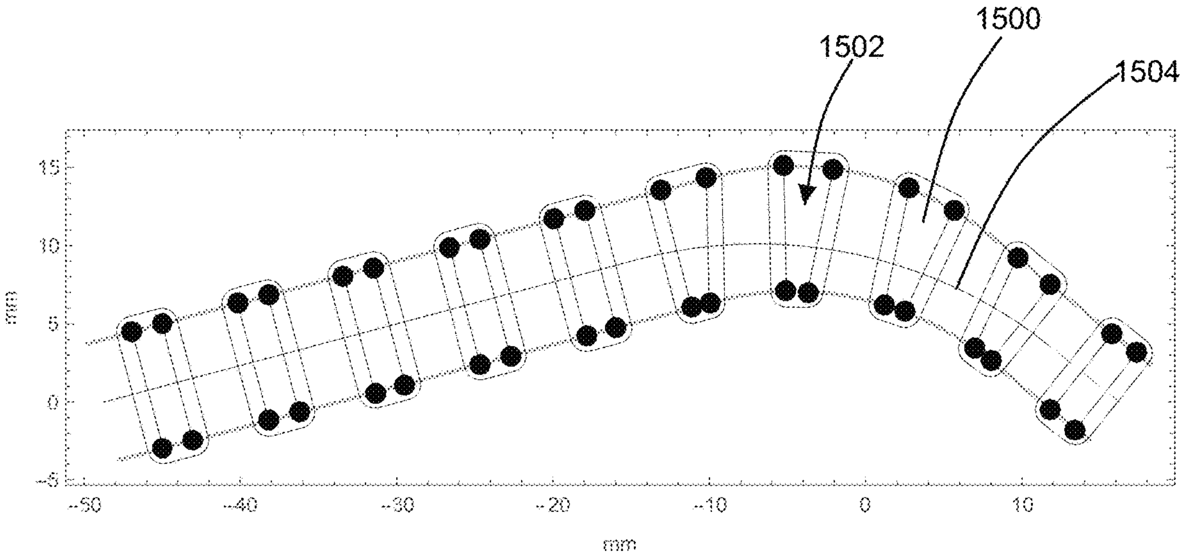
FIG. 21 depicts a top plan view of an asymmetrical template with apertures.

It will be understood that the templates 1402, 1406 shown in FIGS. 18-20 illustrate templates that are tailored to an exact eyebrow shape. Accordingly, apertures on tailored templates, such as the primary and secondary apertures 1404, 1408, may be increased or reduced in height (especially along the tapered tail) to fit the eyebrow shape. Referring to FIG. 21, because eyebrow shapes are so variable, in one embodiment, a general template 1500 can be constructed by extending (or at least not decreasing) the heights of general apertures 1502 along a camber line 1504.

When marking an eyebrow in preparation for a TEPR treatment, tegulae are only marked over inked skin. Even though covering template apertures, such as the primary, secondary, and general apertures 1404, 1408, 1502, may extend significantly beyond the tattooed eyebrow, the actual treated tegulae will only extend as far as the ink. Any extended height apertures simply enable the template to fit greater varieties of inked shapes. Furthermore, tailored templates by their very nature are asymmetric and, therefore, cannot fit both left and right eyebrows. Two right-left mirrored templates would be used to separately fit left and right eyebrows.

Figure 22:
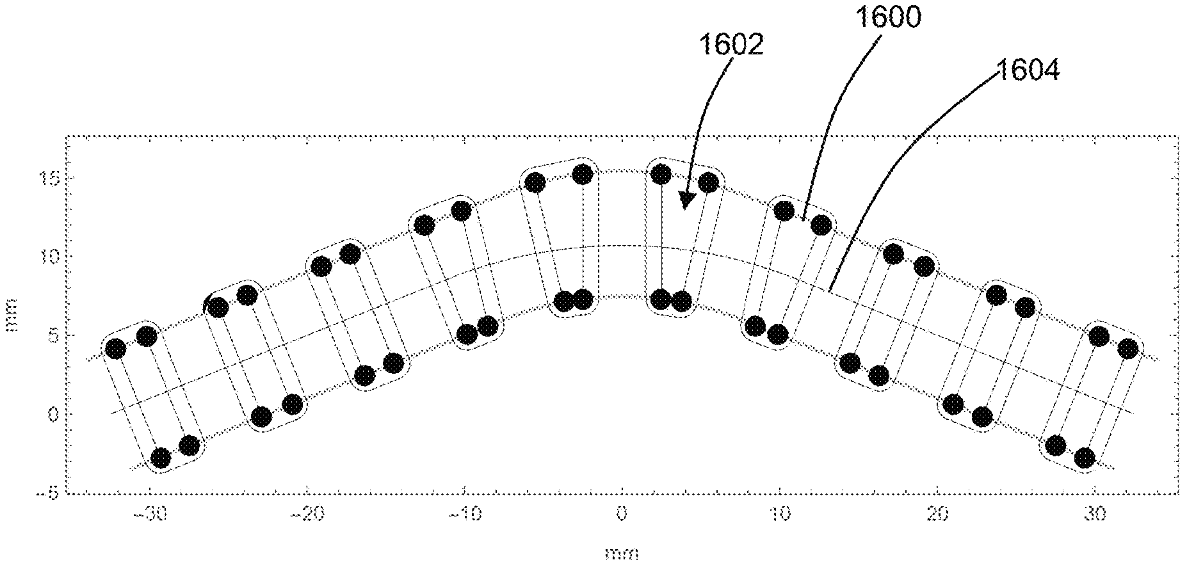
FIG. 22 depicts a top plan view of a symmetrical template with apertures.

In some embodiments, as shown in FIG. 22, a single template, or a symmetric template 1600, fits both right and left eyes equally well. The symmetric template may comprise apertures 1602. The symmetric template 1600 may be constructed from a camber line 1604, characterized by one dimensionless parameter: maximum height to length. This being the case, two or three symmetric templates with different cambers (maximum height to length ratio) may cover a wide variety of eyebrow shapes.

Figure 23:
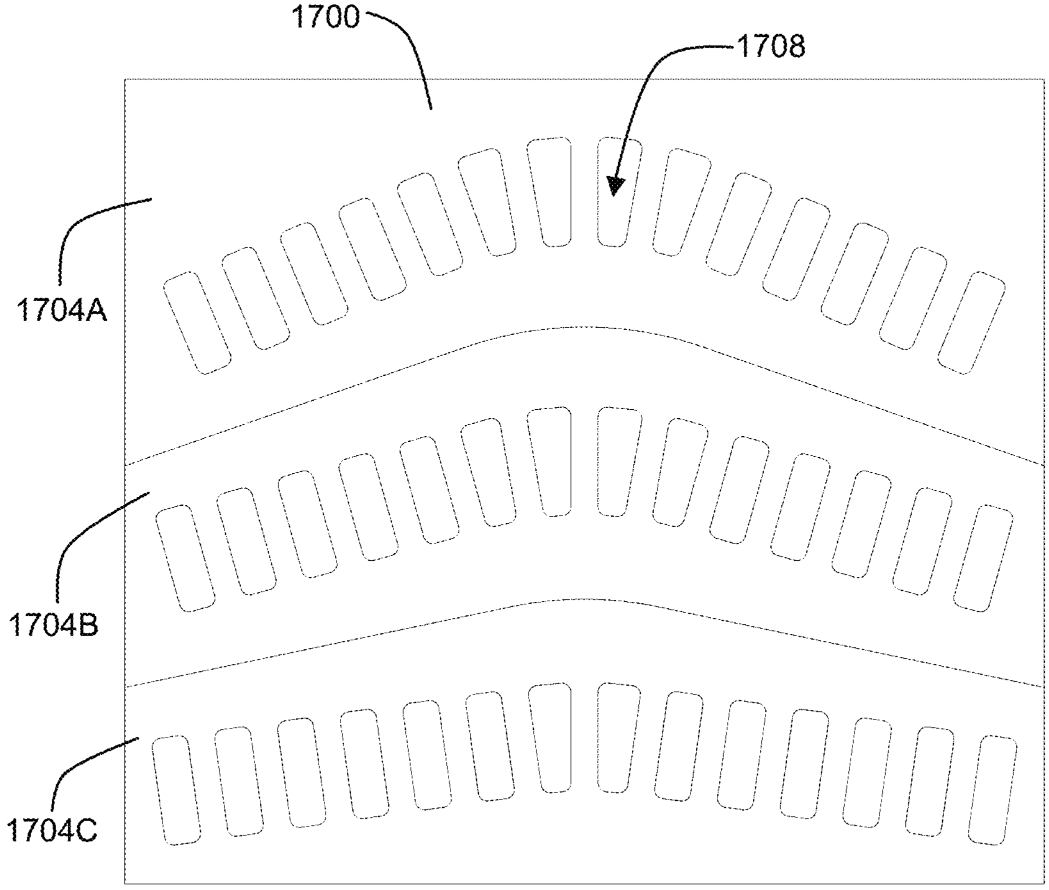
FIG. 23 depicts a top plan view of a first tri-template with multiple templates.
Figure 24:
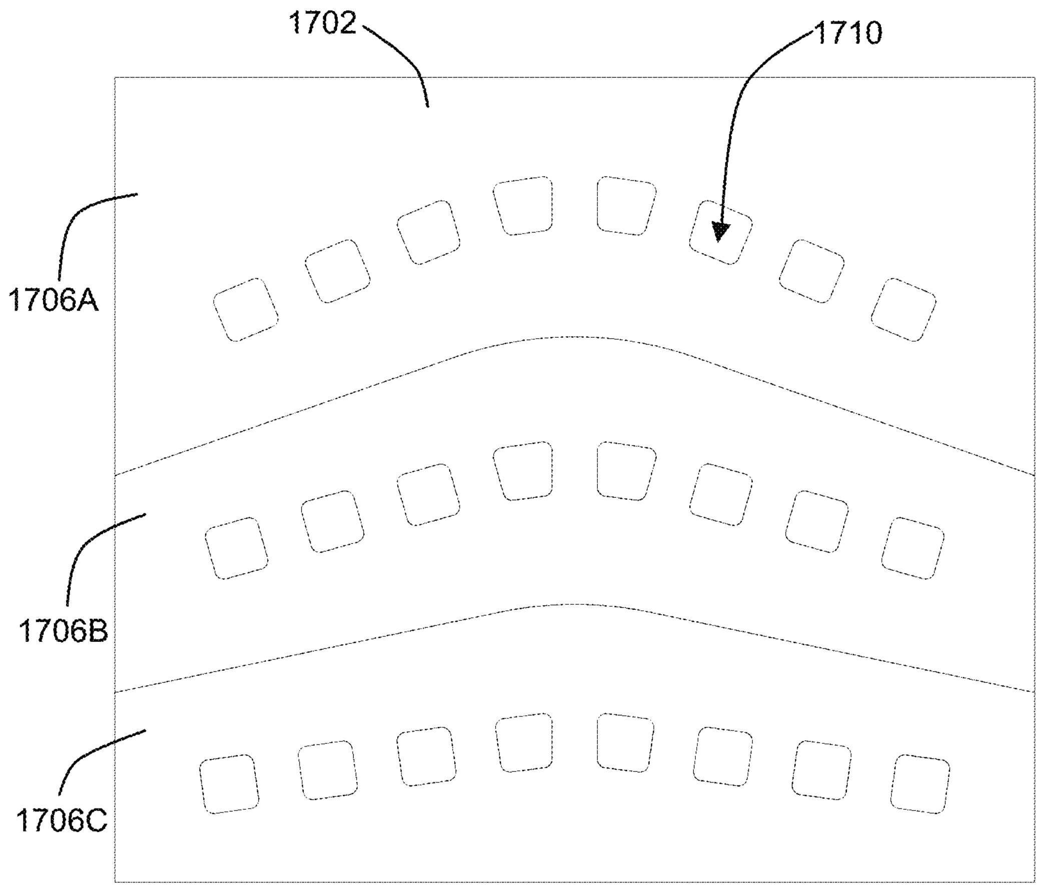
FIG. 24 depicts a top plan view of a second tri-template with multiple templates.

Because of the tent like shape of the symmetric template 1600, templates can by nested one upon another. For example, as illustrated in FIG. 23-24, multiple symmetric templates may be nested to create a first and a second tri-template 1700, 1702. In one embodiment, the first and second tri-templates 1700, 1702 comprise a rectangle 4.0 inches wide by 3.5 inches high. Each tri-template 1700, 1702 consists of three templates, any one of which can be peeled off and used independently. Specifically, the first tri-template 1700 comprises three tall eyebrow templates 1704A-1704C, and the second tri-template 1702 comprises three short eyebrow templates 1706A-1706C. While three templates are shown, it will be appreciated that some nested templates comprise two or more templates. Each template in the first tri-template 1700 comprises similar sized and shaped apertures. However, the apertures differ between the templates in a tri-template set due to the camber of the camber line. In some embodiments, the camber increases as the templates are stacked one upon another in the first and second tri-templates 1700, 1702. As an example, the least cambered template may be at the bottom of the first and second tri-templates 1700, 1702. For example, template 1704C and 1706C may be the least cambered templates.

The first tri-template 1700 illustrated in FIG. 23 is designed to treat tall eyebrows (or thicker, depending on what one calls the vertical extension of eyebrows), such as eyebrows up to 10 mm tall. Accordingly, the first tri-template 1700 comprises first apertures 1708 that may be narrow with rectangular areas. In one embodiment, the rectangular areas do not exceed 40 $mm^2$. As a result, the tri-template 1700 comprises tall and narrow apertures.

Referring to FIG. 24, the second tri-template 1702 comprises second apertures 1710 that are shorter than the first apertures 1708. In one embodiment, the second apertures 1710 comprise a rectangular aperture area of 36 $mm^2$. The second tri-template 1702 may be used to treat shorter eyebrows (or narrower, depending on what one calls the vertical extension of eyebrows). In one embodiment, the second apertures 1710 may comprise a height and width of 6 mm and gaps between the second apertures 1710 may be spaced 5 mm. Accordingly, there may be fewer apertures on the second tri-template 1702 than the first tri-template 1700.

Both the first and the second tri-templates 1700, 1702 treat tattooed eyebrows that are tall or short and have the same range of camber.

When using covering templates as those described above to mark treatment tegulae, the vertical extension of marked tegulae never substantially exceeds the height of the inked skin. Template apertures provide the width and position of tegulae, and a maximum limit on their height, while the inked skin determines their precise vertical extent.

Each of the previously discussed covering templates may comprise a sheet of material, which may be made of silicone, polypropylene, or any other material. In some embodiments, the sheet of material may be flexible to conform to a non-flat surface of a patient's face. In some embodiments, the sheet of material may be flexible while not stretching. The sheet of material may comprise an adhesive layer on a lower surface of the sheet of material, which allows the covering templates to be held in place while marking the tegulae. The adhesive layer may comprise any suitable adhesive. For example, the adhesive layer may be an acrylate, including methacrylates and epoxy diacrylates. Alternatively, the adhesive layer may be a silicone based adhesive. The adhesive layer may be coextensive with the lower surface, in a pattern, or any other manner on the lower surface.

In some embodiments, separate adhesives or tapes may be used to hold the template in place. In some embodiments, tension bands or straps are used to hold the template in place, or any other mechanism for quickly, securely, and easily attaching the template to the patient. Further, a release liner may releasably adhere to the adhesive layer. The release liner may protect the adhesive layer from prematurely adhering to an undesired location and may be removed from the template prior to application on the epidermis. Once the release liner is removed, a user may place the covering template on a patient to mark the tegulae. After the tegulae are marked, the user may either removed the covering template to start the treatment or may leave the template to act as a guide during treatment. Further, in some instances, a user may hold the template with their non-dominant hand while marking the tegulae with their dominant hand. Alternatively, a user may hold and support the template by using a handle device.

In the above description, certain terms may be used such as "up," "down," "upwards," "downwards," "upper." "lower," "horizontal," "vertical," "left," "right," "over." "under and the like. These terms are used, where applicable, to provide Some clarity of description when dealing with relative relationships. But, these terms are not intended to imply absolute relationships, positions, and/or orientations. For example, with respect to an object, an "upper" surface can become a "lower surface simply by turning the object over. Nevertheless, it is still the same object. Further, the terms "including," "comprising," "having," and variations thereof mean "including but not limited to unless expressly specified otherwise. An enumerated listing of items does not imply that any or all of the items are mutually exclusive and/or mutually inclusive, unless expressly specified otherwise. The terms "a," "an, and "the also refer to "one or more' unless expressly specified otherwise. Further, the term "plurality' can be defined as "at least two."

Additionally, instances in this specification where one element is "coupled to another element can include direct and indirect coupling. Direct coupling can be defined as one element coupled to and in some contact with another element. Indirect coupling can be defined as coupling between two elements not in direct contact with each other but having one or more additional elements between the coupled elements. Further, as used herein, securing one element to another element can include direct securing and indirect securing. Additionally, as used herein, "adjacent does not necessarily denote contact. For example, one element can be adjacent another element without being in contact with that element.

As used herein, the phrase "at least one of when used with a list of items, means different combinations of one or more of the listed items may be used and only one of the items in the list may be needed. The item may be a particular object, thing, or category. In other words, "at least one of means any combination of items or number of items may be used from the list, but not all of the items in the list may be required. For example, "at least one of item A, item B, and item C may mean item A; item A and item B; item B; item A, item B, and item C.; or item B and item C. In some cases, "at least one of item A, item B, and item C may mean, for example, without limitation, two of item A, one of item B, and ten of item C: four of item B and seven of item C; or some other suitable combination.

Unless otherwise indicated, the terms "first," "second,' etc. are used herein merely as labels, and are not intended to impose ordinal, positional, or hierarchical requirements on the items to which these terms refer. Moreover, reference to, e.g., a second item does not require or preclude the existence of, e.g., a "first or lower-numbered item, and/or, e.g., a "third" or higher-numbered item.

As used herein, a system, apparatus, structure, article, element, component, or hardware "configured to perform a specified function is indeed capable of performing the specified function without any alteration, rather than merely having potential to perform the specified function after further modification. In other words, the system, apparatus, structure, article, element, component, or hardware "configured to perform a specified function is specifically selected, created, implemented, utilized, programmed, and/or designed for the purpose of performing the specified function. As used herein, "configured to denotes existing characteristics of a system, apparatus, structure, article, element, component, or hardware which enable the system, apparatus, structure, article, element, component, or hardware to perform the specified function without further modification. For purposes of this disclosure, a system, apparatus, structure, article, element, component, or hardware described as being "configured to perform a particular function may additionally or alternatively be described as being "adapted to and/or as being "operative to perform that function.

The schematic flow chart diagrams and method schematic diagrams described above are generally set forth as logical flow chart diagrams. As such, the depicted order and labeled steps are indicative of representative embodiments. Other steps, orderings and methods may be conceived that are equivalent in function, logic, or effect to one or more steps, or portions thereof, of the methods illustrated in the schematic diagrams.

Additionally, the format and symbols employed are provided to explain the logical steps of the schematic diagrams and are understood not to limit the scope of the methods illustrated by the diagrams. Although various arrow types and line types may be employed in the schematic diagrams, they are understood not to limit the scope of the corresponding methods. Indeed, some arrows or other connectors may be used to indicate only the logical flow of a method. For instance, an arrow may indicate a waiting or monitoring period of unspecified duration between enumerated steps of a depicted method. Additionally, the order in which a particular method occurs may or may not strictly adhere to the order of the corresponding steps shown.

The present subject matter may be embodied in other specific forms without departing from its spirit or essential characteristics. The described embodiments are to be considered in all respects only as illustrative and not restrictive. All changes which come within the meaning and range of equivalency of the claims are to be embraced within their scope.

In the above description, specific details of various embodiments are provided. However, some embodiments may be practiced with less than all of these specific details. In other instances, certain methods, procedures, components, structures, and/or functions are described in no more detail than to enable the various embodiments of the invention, for the sake of brevity and clarity.

Although specific embodiments of the invention have been described and illustrated, the invention is not to be limited to the specific forms or arrangements of parts so described and illustrated. The scope of the invention is to be defined by the claims appended hereto and their equivalents.

What is claimed is:

1. A method for removing a skin marking using dermal disruption, the method comprising:

scanning an area of skin of a patient to be treated, wherein the area of skin has not previously undergone dermal disruption to remove the skin marking;

determining a first treatment area of skin of a patient using a primary template, the primary template providing indicia upon the patient's skin defining primary tegulae, wherein a diameter of the primary tegulae is calculated based at least in part on information regarding pigmentation determined by the scan;

disrupting the tissue in the primary tegulae to form a first eschar in a first treatment session;

determining a second treatment area of skin for treatment subsequent to treatment of the first treatment area using a secondary template, the secondary template marking secondary tegulae interposed between primary tegulae; and disrupting the tissue in the secondary tegulae to form a second eschar in a second treatment session.

2. The method of claim 1, wherein disrupting the tissue in the secondary tegulae isolates a plurality of remaining skin marking areas in a grid of tertiary tegulae, and wherein the method further comprises disrupting the tissue in the tertiary tegulae in a third treatment session.

3. The method of claim 1, wherein the secondary tegulae are non-circular and non-polygonal.

4. The method of claim 1, wherein the primary template comprises a flexible, non-stretchable sheet of material.

5. The method of claim 1, wherein the primary template comprises an image projected upon the patient's skin.

6. The method of claim 1, wherein the step of disrupting the tissue comprises applying a mechanical disruption of the tissue.

7. The method of claim 1, wherein the step of disrupting the tissue comprises applying a temperature change to the tissue.

8. The method of claim 7, wherein a temperature of a probe used in applying the temperature change is used to control the depth of tissue disruption at least in part.

9. The method of claim 1, wherein the step of disrupting the tissue comprises applying a chemical agent to the tissue.

10. The method of claim 1, wherein the step of disrupting the tissue comprises applying radiation to the tissue.

11. The method of claim 10, wherein the primary template comprises a reflective portion that resisting energy deposition in an area covered by the reflective portion.

12. The method of claim 1, wherein the step of disrupting the tissue comprises applying focused waves to the tissue.

13. The method of claim 12, wherein a frequency of the focused waves is used to control the depth of tissue disruption at least in part.

14. The method of claim 1, wherein the step of disrupting the tissue comprises applying focused particles to the tissue.

15. The method of claim 1, wherein disrupting the tissue comprises applying variable energy to the area to be treated, and wherein less pigmented areas receive relatively less energy than more deeply pigmented areas.

16. The method of claim 1, wherein natural features of the area to be treated are used as registration marks to orient the primary template.

17. A method for removing a skin marking using dermal disruption, the method comprising:

scanning an area of skin of a patient to be treated, wherein the area of skin has not previously undergone dermal disruption to remove the skin marking;

providing indicia indicative of a template on skin of a patient, the template comprising indicia of a primary lattice tegulae between secondary tegulae;

disrupting the tissue within the primary lattice tegulae to form a first eschar in a first treatment session that isolates the secondary tegulae;

disrupting the tissue in the secondary tegulae to form a second eschar in a second treatment session subsequent to the first treatment session;

wherein a diameter of each of the primary lattice tegulae is calculated based at least in part on information regarding pigmentation determined by the scan.

18. The method of claim 1, wherein the skin marking comprises a tattoo.

19. The method of claim 1, wherein the skin marking comprises a skin irregularity.

20. The method of claim 19, wherein the skin irregularity comprises a skin lesion.

21. The method of claim 19, wherein the skin irregularity comprises stretch marks.

* * * * *